United States Patent
Beri et al.

(10) Patent No.: US 6,258,547 B1
(45) Date of Patent: Jul. 10, 2001

(54) NUCLEIC ACID ENCODING AMP-ACTIVATED PROTEIN KINASE

(75) Inventors: Rajinder Kumar Beri, Macclesfield; David Carling, London; Robert Anthony Forder, Macclesfield, all of (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 08/557,006

(22) PCT Filed: May 20, 1994

(86) PCT No.: PCT/GB94/01093

§ 371 Date: Mar. 6, 1996

§ 102(e) Date: Mar. 6, 1996

(87) PCT Pub. No.: WO94/28116

PCT Pub. Date: Dec. 8, 1994

(30) Foreign Application Priority Data

May 21, 1993 (GB) .................................... 9310489
Aug. 31, 1993 (GB) .................................... 9318010

(51) Int. Cl.[7] .............................. C12Q 1/00; C12N 9/00; A61K 35/14; C07H 17/00
(52) U.S. Cl. .......................... 435/7.1; 435/69.1; 435/183; 530/325; 530/300; 530/350; 530/387.1; 536/23.2; 536/23.4
(58) Field of Search ............................. 435/69.1, 172.3, 435/320.1, 194, 7.1, 183; 536/23.2, 23.5, 23.4; 530/387.1, 326, 300, 350

(56) References Cited

FOREIGN PATENT DOCUMENTS

WO 88/03164    5/1988   (WO) .

OTHER PUBLICATIONS

CARLING, et al: "Purification and characterisation of AMP–activated protein kinase", EUR.J.BIOCHEM., vol 186, No. 1–2, 1989, pp. 129–136, see the whole document.

CELENZA, et al: "A yeast gene that is essential for release from glucose repression encodes a protein kinase", SCIENCE, vol 233, 1986, pp. 1175–1180, see the whole document.

CARLING, et al: "Mammalian AMP–activated protein kinase is homologous to yeast and plant protein kinases involved in regulation of carbon metabolism", J. BIOL. CHEM., vol 269, No. 15, 1994, pp. 11442–11448.

Stapleton, D. et al. *J. Biol. Chem.* 271(2):611–614 (1996).*

Tavare et al. (1985) Biochem. Soc. Trans. 13:734–735. "Insulin–activated acetyl CoA carboxylase Kinase in Triton Extracts of Human Placenta Membranes".*

Beg et al. (1984) Bioc Biop Res Comm. 119:488–498. "Human Hepatic 3–Hydroxy–3–Methylglutaryl Coenzyme a reductase: Evidence for the . . . ".*

S.P. Davies et al, "Tissue Distribution of the Amp–Activated Protein Kinase, and Lack of Activation by Cyclic–Amp–Dependent Protein Kinase, Studied using a Specific and Sensitive Peptide Assay", Eur. J. Biochem., vol. 186, pp. 123–128, 1989.

D. Grahame Hardie et al, "Amp–Activated Protein Kinase–An Archetypal Protein Kinase Cacade?", BioEssays, vol. 14, No. 10, Oct. 1992, pp. 699–704, Oct. 1992.

K.I. Mitchelhill et al, "Mammalian Amp–Activated Protein Kinase Shares Structual and Functional Homology with the Catalytic Domain of Yeast Snf1 Protein Kinase", J. of Biol. Chem., vol. 269, No. 4, pp. 2361–2364, Jan. 1994.

* cited by examiner

Primary Examiner—Karen Cochrane Carlson
(74) Attorney, Agent, or Firm—Pillsbury Madison & Sutro, LLP Intellectual Property Group

(57) ABSTRACT cDNAs encoding mammalian AMP protein kinases, corresponding polypeptides and recombinant proteins together with antibodies thereto. Their uses including the study of gene expression and the characteristics of other proteins.

20 Claims, 20 Drawing Sheets

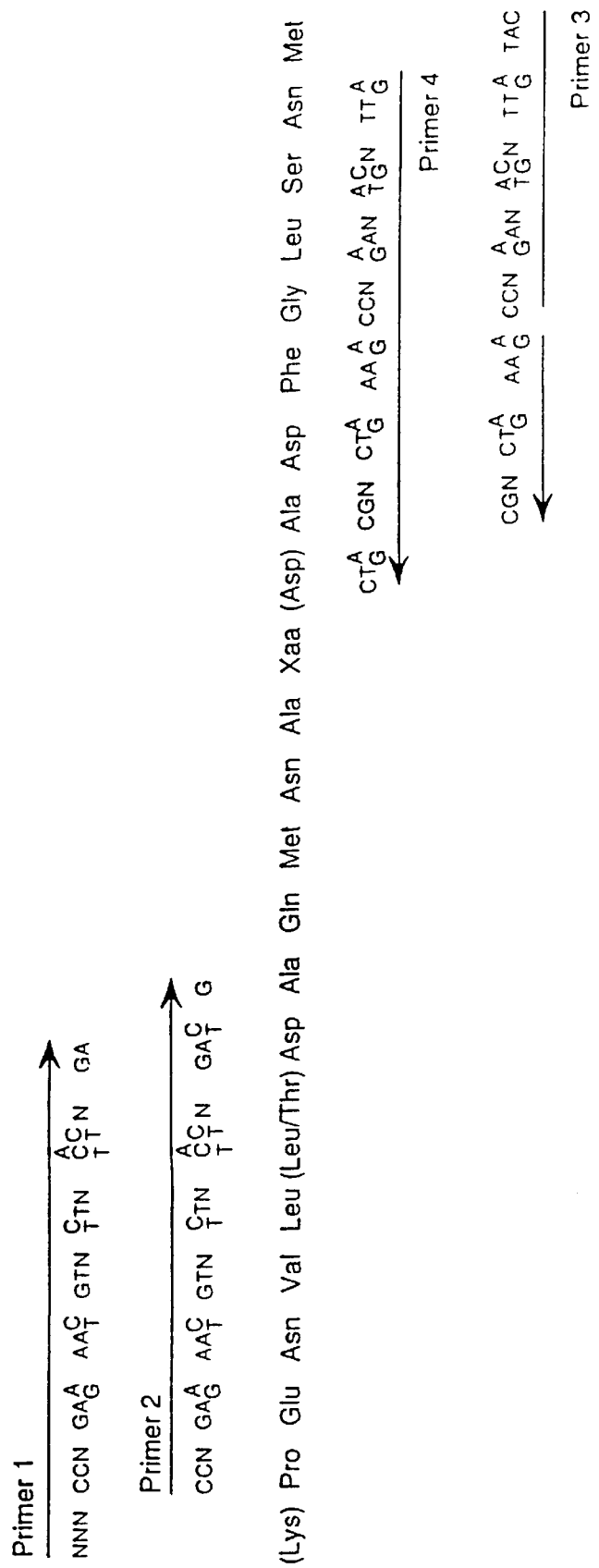

Fig. 3A1

```
1   gccgaacacatggctgagaagcagaagcacgacgggcgtgtgaagatcggacacactacgtgctgggggacac
    M   A   E   K   Q   K   H   D   G   R   V   K   I   G   H   Y   V   L   G   D   T      21

70  cctggggcgtcggcacttcggcaaagtgaagattgaagatggagaacatcaattgacaggccataaagtggcagt
    L   G   V   G   T   F   G   K   V   K   I   G   E   H   Q   L   T   G   H   K   V   A   V     44

139 taagatcttaaatagacagaagattcgcagttagatgtgtgttggaaaataaacgagaaattcaaaa
    K   I   L   N   R   Q   K   I   R   S   L   D   V   V   G   K   I   K   R   E   I   Q   N     67

208 tccttaaacctttcgtcatcctcatattatcaaactccaagtgatcagcactccaacagacttttt
    L   K   L   F   R   H   P   H   I   K   L   Y   Q   V   I   S   T   P   T   D   F   F      90

277 tatgtaatggaatatgtgtctcagggtgaattgttccagattgttctgactacatctgtaaacacgggaggggttgaaga
    M   V   M   E   Y   V   S   G   E   L   F   D   Y   I   C   K   H   G   R   V   E     113

346 ggtgaagctcgccggctcttccagcgattctgtcgcctgtgactactgtcacaggcacatggttgt
    V   E   A   R   R   L   F   Q   Q   I   L   S   A   V   D   Y   C   H   R   H   M   V     136

415 ccacagggacctgaagccagagaacgtgttgctggacgcccagatgaatgcaaagatagctgacttcgg
    H   R   D   L   K   P   E   N   V   L   L   D   A   Q   M   N   A   K   I   A   D   F   G    159

484 actctctaatatgatgtcagatggtgaattctacgaactagctgtgatccaaattatgcagcacc
    L   S   N   M   M   S   D   G   E   F   L   R   T   S   C   G   S   P   N   Y   A   A   P    182

553 ggaggtcatctcaggaaggctgtatgccgggtcgacgtcctgagggtgatatctggagctgtgttatcctgta
    E   V   I   S   G   R   L   Y   A   G   P   E   V   D   I   W   S   C   G   V   I   L   Y    205

622 tgcccttctctgtggcacccctgacgatgagcacgtgcctacgtctcttaagagatccgagg
    A   L   L   C   G   T   L   P   F   D   D   E   H   V   P   T   L   F   K   K   I   R   G    228

691 gggtgttctacatcccggagtatctccaaccgttctattgccactctgctgatgcacatgctgcaggt
    G   V   F   Y   I   P   E   Y   L   N   R   S   I   A   T   L   L   M   H   M   L   Q   V    251

760 ggaccccctgaagcgagcaactatcaaagacatacgagagcatgaatggtttaaacaggatttgcccag
    D   P   L   K   R   A   T   I   K   D   I   R   E   H   E   W   F   K   Q   D   L   P   S    274

829 ttacctctttcctgaagaccctctatgatgctaacgtcattgatgaggctgtgaaagaagtatg
    Y   L   F   P   E   D   P   S   Y   D   A   N   V   I   D   D   E   A   V   K   E   V   C    297

898 tgaaaaattggtgtacagtgatgaaacagtttatacagtggtgaccctcaagaccagat
    E   K   F   E   C   T   E   S   E   V   M   N   S   L   Y   S   G   D   P   Q   D   Q   L    320
```

Fig. 3A2

```
 967 cgcagtggcttatcatccatcattgacaatcgagaataatgaaccaagccagtggagttctacctcgc        343
      A V A Y H L I I D N R R I M N Q A S F F Y L A
1036 ctccagtcctccaacggttccttcatgacgatatggccatgcacatccccccggcctgaaaccaca        366
      S S P P T G S F M D D M A M H I P G L K P H
1105 tcctgaaaggatgccacctcctcatagcagacagcccaaagcacgctgtccactgatgcactcaacac      389
      P E R M P P L I A D S P K A R C L D A L N T
1174 aactaagcccaaatctttagctgtgaaaaaagccaagtggcaccttgggatccgaagccagagcaaacc     412
      T K P K S L A V K K A K W H L G L P S Q S K P
1243 atacgacattatgcggaggtgtaccgagctatgaagcagctgggactttgaatggaagtagtgaatgc     435
      Y D I M A E V Y R A M K Q L D F E W K V V N A
1312 ataccatcttcgagtaagaagaaaaaccagtgactggcaattacgtgaaaatgagcttacagcttta      458
      Y H L R V R R K N P V T G N Y V M S L Q L Y
1381 cctgttgacaatcggagctatcttcagacttaaaagcatcgatgatgaggtggtggagcagaggtc       481
      L V D N R S Y L L D F K S I D D E V V E Q R S
1450 tggttcttcaacacctcagcgctcctgtctcgctgccggctccacagacctcggtcaagtgtcgattc     504
      G S S T P Q R S C S A A G L H R P R S S V D S
1519 cagcacagccgagaaccattcactgtctgctctcactggttcttgaaatgtgccagtcttatcactgctt    527
      S T A E N H S L S G S L T G S L T G S T L S S
1588 cgcttcccccgcctggcagtcagtaccaccgtgattttttgaaatgtgccagtcttatcactgctt        550
      A S P R L G S H T M D F F E M C A S L I T A L
1657 agcccgttgataaccaccacggtctctgtcttctgttaccgcactgtgaaatcacatacactcttc       552
      A R
1726 aaattattaccgcactctcgggtaccacaggctctgcaatagaagttatgtgaactattccaggtgaca
1795 tgcagtgctgctgaaacacagaaatctgccttcgtgttactttagaactctgtaactctgtgtgc
1864 ctatgataggtatcaatagctaggaacgctaggaacgcttgttgtgaagcttgttaacttacacccgtgaatt
1933 cactacacatggtgagcacaccagtaaccctactaatcctcactgatgaaccctcggggtggttcggtgggaccgcctt
2002 cctcacgttagtctcatgtaaatccgtgcctcctaaatttgcctcataggtgtcaggctgtctaggca
2071 ctcttggacaagaagattcagaaatagagtaactgtcagtgaaatagaaccaaagtctttttaatactttctgcaaatactgcctagtat
2140 aatcctgtccctttaaatatcagaaccaatagaaccaaagtcttttttaatactttctgacatttgtcaaggcc
2209 tagccataacagactgtgttctgataaagcaatataagcaataaaaccatgcaaagttagtgcatagtaaagggaaaca
2278 cctagtaaatccactacagtctcttaaagaaatctattcttttgatctcattgtgttttatgagactggta
2347 gcagatacaacagtctcttggggctcacactcacctgttggacatcttggcaatccacttgaactttttgt
2416 gctggggcttggggcggtcctctcttccctcagtagccactggccatggtgcaatccacttgaactttttgt
2485 tattgatgccgatccctcttcttccttggccataggtctttaaatactttcaaagcttcaaagcttcaaagcttcatctgctgtgac
2554 tcctttagatcaaaacctgtcttggccataggtctttaaatactttcaaagcttgatctgctgtgac
2623 cttcactgttgaacctgattgacagggaa 2652
```

1   atggctgagaagcagaagcacgacgggcgtgtgaagatcggacactacgtgctgggggac

1   M  A  E  K  Q  K  H  D  G  R  V  K  I  G  H  Y  V  L  G  D 142 bp deletion 60  accctgggcgtcggcaccttcggcaaagtgaagactaccaagtga

```
AMPK
SNF1   M S S N N N T N T A P A N A N S S H H H H H H H H H H H H H G H G G S N S T L

AMPK   M A E K Q K H D G R V K I G H Y V L G D T L G V G T F G K V K I G E H Q L T G
SNF1   N N P K S S L A D G A H I G N Y Q I V K T L G E G S F G K V K L A Y H T T T G

AMPK   H K V A V K I L N R Q K I R S L D V V G K I K R E I Q N L K L F R H P H I I K
SNF1   Q K V A L K I I N K K V L A K S D M Q G R I E R E I S Y L R L L R H P H I I K

AMPK   L Y Q V I S T P T D F F M V M E Y V S G G E L F D Y I C K H G R V E E V E A R
SNF1   L Y D V I K S K D E I I M V I E Y   A G N E L F D Y I V Q R D K M S E Q E A R

AMPK   R L F Q Q I L S A V D Y C H R H M V V H R D L K P E N V L L D A Q M N A K I A
SNF1   R F F Q Q I I S A V E Y C H R H K I V H R D L K P E N L L L D E H L N V K I A

AMPK   D F G L S N M M S D G E F L R T S C G S P N Y A A P E V I S G R L Y A G P E V
SNF1   D F G L S N I M T D G N F L K T S C G S P N Y A A P E V I S G K L Y A G P E V

AMPK   D I W S C G V I L Y A L L C G T L P F D D E H V P T L F K K I R G G V F Y I P
SNF1   D V W S C G V I L Y V M L C R R L P F D D E S I P V L F K N I S N G V Y T L P

AMPK   E Y L N R S I A T L L M H M L Q V D P L K R A T I K D I R E H E W F K Q D L P
SNF1   K F L S P G A A G L I K R M L I V N P L N R I S I H E I M Q D D W F K V D L P

AMPK   S Y L F P E D                             P S Y D A N V I D D E A V K
SNF1   E Y L L P P D L K P H P E E E N E N N D S K K D G S S P D N D E I D D N L V N

AMPK   E V C E K F E C T E S E V M N S L Y S G D P Q       D Q L A V A Y H L I I D N
SNF1   I L S S T M G Y E K D E I Y E S L E S S E D T P A F N E I R D A Y M L I K E N

AMPK   R                 R I M N Q A S E F Y L A S S P P T
SNF1   K S L I K D M K A N K S V S D E L D T F L S Q S P P T F Q Q Q S K S H Q K S Q

AMPK                             G S F M D D M A M H I P P G L K P H P E
SNF1   V D H E T A K Q H A R R M A S A I T Q Q R T Y H Q S P F M D Q Y K E E D S T V

AMPK                             R M P P L I A D S P K A R C P L D A L N T K P K S L A V
SNF1   S I L P T S L P Q I H R A N M L A Q G S P A A S K I S P L V T K K S

AMPK   K K A K W H L G I R S Q S K P Y D I M A E V Y R A M K Q L D F E W K V V N A Y
SNF1     K T R W H F G I R S R S Y P L D V M G E I Y I A L K N L G A E W A K P S E E

AMPK   H L         R V R R K                 N P V T G N Y V K M S L Q L Y L V D N R
SNF1   D L W T I K L R W K Y D I G N K T N T N E K I P D L M K M V I Q L F Q I E T N

AMPK   S Y L L D F K S I D D E V V E Q R S G S S T P Q R S C S A A G L H R P R S S V
SNF1   N Y L V D F K   F D G W

AMPK   D S S T A E N H S L S G S L T G S L T G S T L S S A S P R L G S H T M D F F E
SNF1   E S S Y G D D T T V S N I S E D E M   S T F S A Y P             F L H

AMPK   M C A S L I T A L A R
SNF1   L T T K L I M E L A V N S Q S N
```

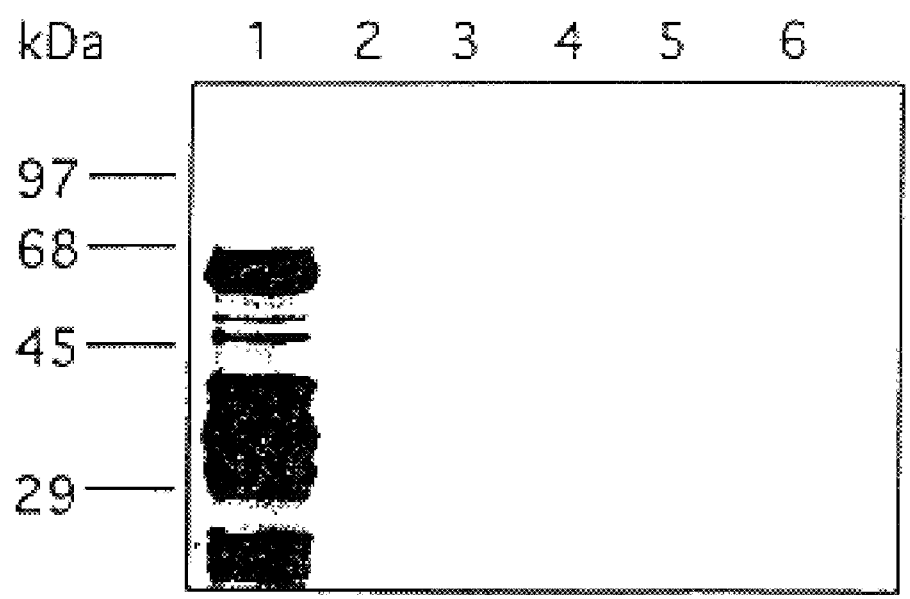

FIG. 8

| PEPTIDE(SIZE) | SEQUENCE |
|---|---|
| PK0(17K/18K) | XLXPENVL(T/L)DA(Q/P)MNAXDADFG(L)SNM |
| BT2(7K) | EYV(Y)G(K/L)(E)LF(A)YIXKXGXXXXV |
| BT3(12K) | LQV(D)PLK(R)ATIK(D)IXE(E)E(W)FKQ |
| BT4(8K) | PPLIADXPKARXPLD(A)LN(T)(T)K |
| BT1(7K/14K) | KQLDFE(W/S)(K/G)KVVNAY(H)L(R)V(R)XKXN |

X = UNCERTAIN
( ) = MOST LIKELY

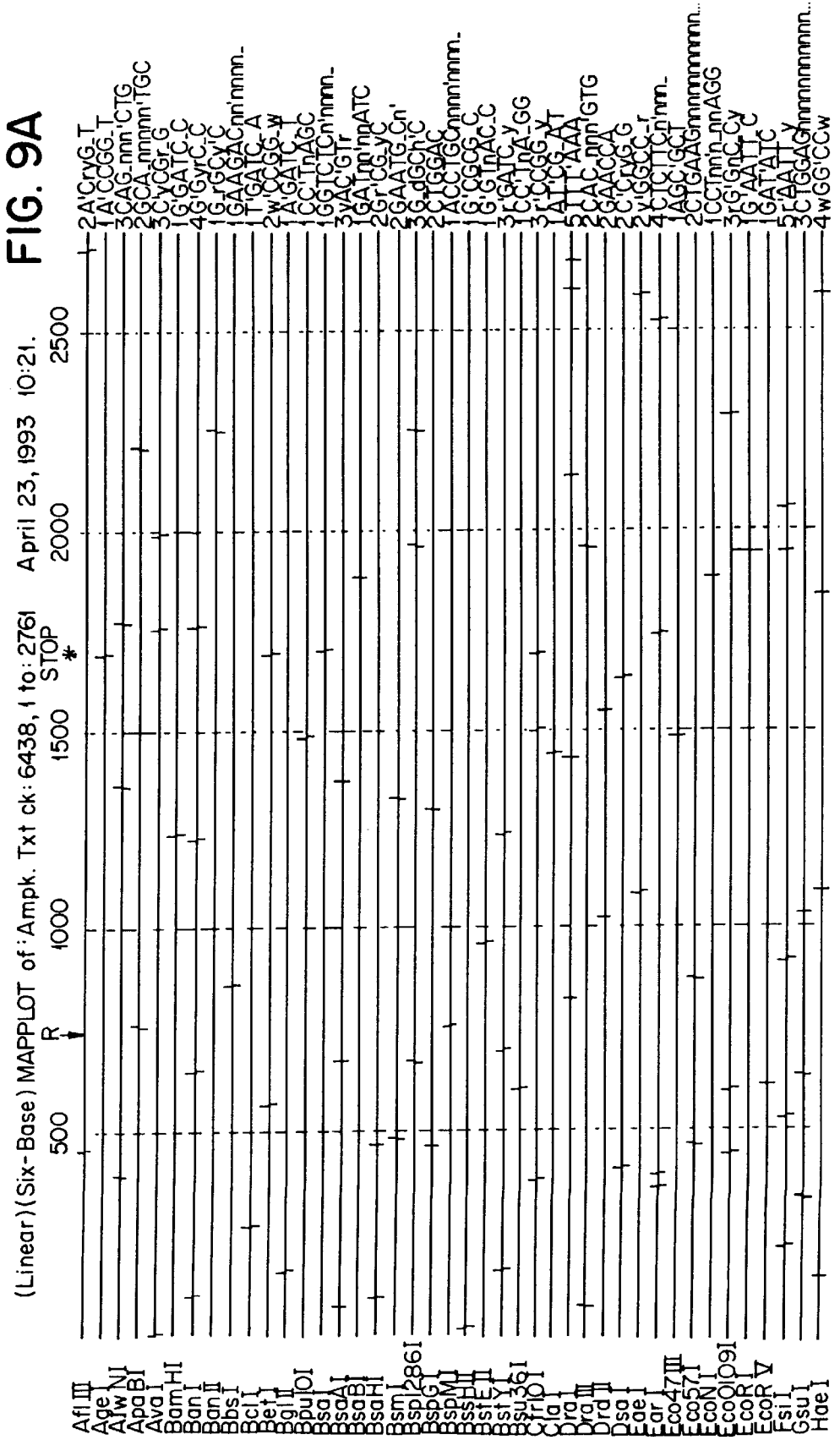

FIG. 10

Amino Acid Sequence Information Obtained from Peptides Derived from AMPK

| Method of Cleavage Comments | Peptide | Amino Acid Sequence | Comments |
|---|---|---|---|
| Endoproteinase lys C homology to protein kinase subdomains VIb-VII | EL1 | (K) PENVLTDAQMNAX (D) ADFGLSNM<br>    L           KI | homology to protein subdomains VIb-VII |
| S.aureus V8 protease sequence derived from peptide | SV1<br>EL1 | (E) NVL (L/T) DAQMNAX (D) ADFGLSNM<br>       L              K    I | sequence derived from peptide |
| S.aureus V8 protease | SV2 | (E) FYLA | |
| Cyanogen bromide homology to protein kinase subdomain V | CB1 | (M) EYVSGGELFDYICKHGREVEE | homology to protein kinase subdomain V |
| Cyanogen bromide | CB2 | (M) PPLIADSPKARCPLDALNTTK | |
| Cyanogen bromide | CB3 | (M) KQLDFEWKVVNAYHRVRRK | |

FIG. 11A

```
  2 ATGGCTGAGAAGCAGAGAAGCACGACGGGCGGGGTGAAGATCGGACACTACGT  51
    |||||||||||||||||||||||||||||||||||||||||||||||||||
 24 ATGGCTGAGAAGCAGAGAAGCACGACGGGCGGGGTGAAGATCGGACACTACGT  73

52 GCTGGGCGACACGCTCGGGCGTCGGCACCTTCGGCAAAGTGAAGATTGGAG  101
    |||||||||||||||||||||||||||||||||||||||||||||||||
 74 GCTGGGGGACACCCTCGGGCGTCGGCACCTTCGGCAAAGTGAAGATTGGAG  123

102 AACATCAATTAACAGGCCATAAAGTGGCAGTTAAAATCTTAAATAGACAG  151
    |||||||||||||||||||||||||||||||||||||||||||||||||
124 AACATCAATTGACAGGCCATAAAGTGGCAGTTAAGATCTTAAATAGACAG  173

152 AAGATTCGCAGTTTAGATGTTGTTGAAAAATAAAACGAGAAATTCAAAA   201
    |||||||||||||||||||||||||||||||||||||||||||||||
174 AAGATTCGCAGTTTAGATGTTGTTGAAAAATAAAACGAGAAATTCAAAA   223

202 TCTAAAACTCTTTCGTCATCCTCATATTATCAAACTATACCAGGTGATCA  251
    |||||||||||||||||||||||||||||||||||||||||||||||||
224 TCTTAAACTCTTTCGTCATCCTCATATTATCAAACTCTACCAAGTGATCA  273

252 GCACTCCAACAGAGATTTTTTATGGTAATGGAATATGTGTCTGGAGGTGAA  301
    ||||||||||||||||||||||||||||||||||||||||||||||||||
274 GCACTCCAACAGACTTTTTTTATGGTAATGGAATATGTGTCTGGAGGTGAA  323
```

FIG. IIB

```
302  TTATTTGACTACACATCTGTAAGCATGGACGGGTTGAAGAGATGGAAGCCAG  351
         ||| |||||||||||||||||| ||||| |||||||||||  ||||||||
324  TTGTTTCGACTACACATCTGTAAACACGGGAGGGTTGAAGAGGTGGAAGCTCG  373

352  GCGGCTCTTTCAGCAGATTCTGTCTGCTGGATTACTGTGTCATAGGCATA  401
     || |||||||||||||||||||||| ||||||| |||||||||||| |||
374  CCGGCTCTTCCAGCAGATTCTGTCTGCCGTGGACTACTGTGTCACAGGCACA  423

402  TGGTTGTTCATCGAGACCTGAAACCAGAGAATGTCCTGTTGGATGCACAC  451
     ||||||| |||| |||||||||| |||||||| || || ||||| |||||
424  TGGTTGTCCACAGGGACCTGAAGCCAGAGAACGTGTTGCTGGACGCCCAG  473

452  ATGAATGCCAAGATAGCCGATTTCGGATTATCTAATATGATGTCAGATGG  501
     ||||||||||||||| ||  ||||| |||| |||||||||||||||||||
474  ATGAATGCTAAGATAGCTGACTTCGGACTCTCTAATATGATGTCAGATGG  523

502  TGAATTTCTGAGAACTAGTTGCGATCTCCAAATTATGCAGCACCTGAAG  551
     |||||||||| ||| | |||||| ||||||||||||||||||| ||||
524  TGAATTTCTACGAACTAGCTGTGATCGCCAAATTATGCAGCACCGGAGG  573

552  TCATCTCAGGCAGATTGTATGCAGGTCCTGAAGTTGATATCTGGAGCTGT  601
     |||||||||| |||| ||||||| |||||| ||||||||||||||||||
574  TCATCTCAGGAAGGCTGTATGCGGGTCCTGAGGTTGATATCTGGAGCTGT  623
```

FIG. IIC

```
602  GGTGTTATCTTGTATGCTCTCTTCTTTGTGGCACCCTCCCATTTGATGATGA  651
     ||||||||||||||||||| ||||||  |||| ||||||||||||||||||
624  GGTGTTATCCTGTATGCCCTTCTCTGTGGCACCCTCCCGTTCGACGATGA    673

652  GCATGTACCTACGTTATTTAAGAAGATCCGAGGGGGTGTCTTTTATATCC    701
     ||| ||   |||| ||| ||||| ||||||||| ||||||| || ||||
674  GCACGTGCCTACGCTCTTTAAGAAGATCCGAGGGGTGTTCTACATCC       723

702  CAGAATATCTCAATCGTTCTCGTCGCCACTCTCCTGATGCATATGCTGCAG  751
     | ||  |||||||| ||||||  ||||||||||||||||||| |||||||
724  CGGAGTATCTCAACCGTTCTATTGCGAGCAACTATCAAAGACATAAGAGAGCATGAATG  773

752  GTTGACCCACTGAAACGAGCAACTATCAAAGACATAAGAGAGCATGAATG   801
     || ||||| ||||  |||||||||||||||||||||||||||||||||||
774  GTGGACCCCTTGAAGCGAGCAACTATCAAAGACATACGAGAGCATGAATG   823

802  GTTTAAACAAGATTTGCCCAGTTACTTATTCCTGAAGACCCTTCCTATG    851
     ||||||||| ||||||||||||||| |||| |||||||||| ||||||||
824  GTTTAAACAGATTTGCCCAGTTACCTCTTTCCTGAAGACCCCTCCTATG    873

852  ATGCTAACGTCATTGATGATGAGGCTGTGAAAGAAGTGTGTGAAAAATTT   901
     ||||||||||| |||||||||||||||||||| |||||||||||||||||
874  ATGCTAACGTCATTGATGATGAGGCTGTGAAAGAAGTATGTGAAAAATTT   923
```

FIG. 11D

```
 902 GAATGTACAGAATCAGAAGTAATGAACAGTTTATATAGTGGTGACCCTCA  951
     ||||||||||||||||||| |||||||||||||| ||||||||||||||
 924 GAGTGTACAGAATCAGAAGTGATGAACAGTTTATACAGTGGTGACCCTCA  973

952 AGACCAGCTTGCAGTGGCTTATCATCTTATCATTGACAATCGGAGAATAA 1001
     ||||||||| |||||||||||||||||||||||||||||||||||||||
 974 AGACCAGCTCGCAGTGGCTTATCATCTCATCATTGACAATCGGAGAATAA 1023

1002 TGAACCAAGCCCAGTGAGTTCTATCTCGCCCTCTAGTCCTCCATCTGGTTCT 1051
     |||||||||||||||||||||||||| ||||||| ||||||||| | ||
1024 TGAACCAAGCCCAGTGAGTTCTACCTCGCCCTCCAGTCCTCCAACGGGTTCC 1073

1052 TTTATGGATGATAGTGCCATGCATATTCCCCCCAGGCCTGAAACCTCATCC 1101
       | ||||| ||| |||||||||| ||||||||||||||||||||||||
1074 TTCATGGACGATATGGCCATGCACATTCCCCCGGCCTGAAACCACATCC 1123

1102 AGAAAGGATGCCACCTCTTATAGCAGACAGCCCCAAAGCAAGATGTCCAT 1151
     ||| ||||||||||||||| ||||||||||||||||||||| |||||||
1124 TGAAAGGATGCCACCTCTCATAGCAGACAGCCCCAAAGCACGCTGTCCAC 1173

1174 TGGATGCACTCAACACAACTAAGCCCAAATCTTTAGCTGTGTGAAAAAGCC 1223
```

FIG. 1IE

```
1202  AAGTGGCATCTTGGAATCCGAAGTCAGAGAGCAAACCGTATGACATTATGGC  1251
      ||||||||| ||| |||||||| ||||||||||||||| |||||||||||||
1224  AAGTGGCACCTTGGGATCCGAAGCCAGAGAGCAAACCATACGACATTATGGC  1273

1252  TGAAGTTTACCGAGCTATGAAGCAGCTGGATTTTGAATGGAAGGTAGTGA    1301
      ||||||||||||||||||||||||||||||| ||||||||||||||||||
1274  GGAGGTGTACCGAGCTATGAAGCAGCTGGACTTTGAATGGAAGGTAGTGA    1323

1302  ATGCATACCATCTTCGTGTAAGAAGAAAAAATCCAGTGACTGGCAATTAC    1351
      |||||||||||||||| ||||||||||||| |||||||||||||||||||
1324  ATGCATACCATCTTCGAGTAAGAAGAAAAACCCAGTGACTGGCAATTAC    1373

1352  GTGAAAAATGAGCTTACAACTTTACCTGGTTGATAACAGGAGCTATCTTTT   1401
      ||||||||||||||||||| ||||||||||||| |||||||||||||| |
1374  GTGAAAAATGAGCTTACAGCTTTACCTGGTTGACAATCGGAGCTATCTTCT   1423

1402  GGACTTTAAAAGCATTGATGATGAAGTAGTGGAGCAGAGATCTGGTTCCT    1451
      |||||||||||||||||||||| ||||||||||||||||| |||||||||
1424  AGACTTTAAAAGCATCGATGATGAAGTGGAGCAGAGAGTCTGGTTCTT    1473

1452  CAACACCTCAGCGTTCCTGTTCTGCTGGCTTACACAGACCAAGATCA      1501
      |||||||||||| ||||||||||||||||| ||||||||||||| ||
1474  CAACACCTCAGCCTCCCTGTTCTGCTGCCGGCCTCCACAGACCTCGGTCA   1523
```

FIG. IIF

```
1502  AGTTTTGATTCCACAACTGCAGAGAGCCATTCACTTTCTGGCTCTCTCAC  1551
          ||||||  ||  |||||||||  ||||||||||||||||||||||||||
1524  AGTGTCGATTCCAGCACACAGCCGAGAACCATTCACTGTCTGGCTCTCTCAC  1573

1552  TGGCTCTTTGACCGGAAGCACACATTGTCTTCAGTTTCACCTGCCTGGGCA  1601
      |||  ||||||||||  ||||  ||  ||||||||||||||  ||||||||
1574  TGGTTCTTTGACTGGCAGAACTTGTCCTCCCGCCTTCCCCGGCCTGGGCA  1623

1602  GTCACACCATGGATTTTTTGAAAATGTGTGCCAGTCTGATTACTACTTTA  1651
      |||| ||||||||||||||| ||||||||| |||||||||  |||| |||
1624  GTCATACCATGGATTTTTTTGAAAATGTGCGCCAGTCTTATCACTGCTTTA  1673

1652  GCCCGTTGAT.........CTGTCTCTAGTTTCTTTTCTGTTATTGCACT  1691
      |||||||||||        ||||||     |||     |||||||||||
1674  GCCCGTTGATAACCCACCACCGGTCTC...TGTCTTTCGTTACCGCACT  1720

1692  ATGAAAATCAGTTATATCTTTAAATTTTTATCTTACTTTTTGGATA  1737
      |||  |||||| ||||  ||| ||||  ||  |||  |  ||| ||
1721  GTG.AAATCACATACACTCTTCAAATTATTACCGCACTCTCGGGTA  1765
```

NUCLEIC ACID ENCODING AMP-ACTIVATED PROTEIN KINASE

This application claims benefit of international application PCT/GB94/01093, filed May 20, 1994.

The key enzymes regulating fatty acid and cholesterol biosynthesis in the body are acetyl coA carboxylase (ACC) and HMG CoA reductase (HMG-R). The release of fatty acids and cholesterol from intracellular stores of triglycerides and cholesterol esters is regulated by hormone sensitive lipase (HSL). Regulation of these enzymes is multivalent eg feedback inhibition, transcriptional and translational control. More recently, reversible phosphorylation has also been discovered as a mechanism for the acute regulation of at least ACC and HMG-R, and possibly HSL. Work over the past few years has identified the key kinase that regulates the activities of these enzymes.

AMP protein kinase, which is itself regulated allosterically by 5'-AMP and reversible phosphorylation (by a distinct kinase—kinase), can phosphorylate and inactivate ACC and HMG-R (& possibly HSL). Although agents which inhibit HMG-R, such as members of the statin family of compounds, have found great utility in the clinic for the treatment of hypercholesterolaemia, there are no acceptable agents for the treatment of combined hyperlipidaemia ie elevated fatty acids & elevated cholesterol levels; elevated fatty acids are increasingly being recognised as important in numerous disease states.

Carling et al (Eur. J. Biochem., 1989, 186, 129–136) describe the purification of an AMP protein kinase from rat liver. However, all efforts to clone a mammalian AMP protein kinase appear to have been unsuccessful.

According to a first aspect of the present invention we now provide a cDNA encoding a mammalian AMP protein kinase and convenient fragments thereof. The cDNA is conveniently as set out in Table 1 and a restriction map indicating convenient fragments thereof is set out in Table 3.

In a further aspect of the present invention we provide a recombinant mammalian AMP protein kinase and convenient fragments thereof. This may for example be obtained by expression of the cDNA as set out in SEQ ID NO: 24 or convenient fragments thereof as indicated in FIG. 9. Convenient peptide sequence which may be obtained is set out in FIG. 8. Methods for cDNA expression will be apparent to the molecular biologist of ordinary skill and include those set out in the Maniatis cloning manual (Molecular Cloning: A Laboratory Manual—2nd Edition (1989)—J. Sambrook, E. F. Fritsch & Maniatis), and in Current Protocols in Molecular Biology—1987—P. Sharp (Ed.). Particular expression systems include the mouse erythroleukaemia (mel) cell expression system claimed in WO-89/01517 (Grosveld) and, more particularly, as claimed in WO-92-11380 (Hollis et al). An alternative expression system is the Baculovirus Expression System (Clontech)—A. Prokop et al, Recombinant DNA Technology & Applications, 1991, 97–152.

The recombinant mammalian AMP protein kinase of the present invention is used to identify agents which modulate the action of this kinase. Such agents are desirable since, for example, they can be used to reduce the biosynthesis of cholesterol and fatty acids. They may also be used to inhibit the release of these from intracellular stores by HSL.

Therefore in a further aspect of the present invention we provide a method for the identification of an agent which increases activation of AMP protein kinase, which method comprises contacting a potential agent with a recombinant mammalian AMP protein kinase and identifying any increase in AMP protein kinase activation over that found in the absence of the agent. Any convenient assay format may be used. In particular a peptide, for example containing a serine residue exclusively phosphorylate by AMP protein kinase is incubated in the presence of a preparation of AMP protein kinase and a radiolabel such as gamma 33-P. The reaction is allowed to proceed for a period of about 1 hour and is conveniently terminated by the addition of acid. The phosphorylated peptide is conveniently separated from unicorporated radiolabel by binding to a charged membrane followed by washing. The degree of phosphorylation of the peptide is a measure of the activity/activation of the AMP protein kinase.

In a further aspect of the invention we provide a method for the identification of an agent which increases the level of AMP protein kinase expression, which method comprises contacting a potential agent with a cell expressing a mammalian AMP protein kinase and identifying any increase in the level of AMP protein kinase expression over that found in the absence of the agent. This method may involve the use of any convenient in vitro assay. In general, a cell expressing the mammalian AMP protein kinase gene is contacted with an agent capable of transcriptionally modulating expression of the gene, thereby affecting the level of protein encoded by the gene which is expressed by the cell. Convenient procedures are described in WO90/01379 (Oncogene). An increase in transcription may be monitored by blotting techniques using probes derived from the cDNA encoding the AMP protein kinase, or by PCR using primer sequences derived from the cDNA. Protein expression levels can be conveniently monitored by the use of antibodies and enzyme activity measured as described above.

The cDNA of the invention encoding a mammalian AMP protein kinase, or any convenient fragment thereof, may be used to provide DNA probes. A convenient probe comprises the full cDNA sequence of a mammalian AMP protein kinase, for example the cDNA sequences set out in SEQ ID NO: 24. The molecular biologist of ordinary skill will be aware that the above DNA probes (or RNA probes derived therefrom) may be use in a number of procedures. These include the identification and cloning of homologous mammalian and non-mammalian cDNAs including the associated kinase—kinase. Such homologous cDNAs represent further independent aspects of the invention. They may be cloned into vectors (such as those commercially available) in order to produce useful fusion proteins or cloned into expression vectors to construct high level expressing cell lines. They may also be used in gene cloning studies in order to analyse a number of regulatory elements including promoters, enhancers and introns. In addition they may be used to investigate gene expression in vivo. They may also be used in the preparation of transgenic animals, such as mice or rats.

As outlined earlier above the recombinant mammalian AMP protein kinase of the invention, and convenient fragments thereof, may be used to identify agents which cause increased enzyme activation. It may be used in molecular modelling and X-ray crystallography studies. In addition it can be used to map the site(s) phosphorylated by the putative kinase—kinase (which causes activation of AMP protein kinase) and de-phosphorylated by a kinase-phosphatase (inactivated AMP protein kinase). This is conveniently achieved by working out sequentially (i) the number of sites phosphorylated on the protein (ii) which site(s) are phosphorylated by which protein kinase (in vitro) and (iii) which kinase(s) are responsible for phosphorylation in vivo. Based on the data derived from the above types of experiments, and AMP protein kinase peptide substrate specific for the kinase—kinase and kinase-phosphatase may be developed to allow specific assays for the latter enzymes.

The recombinant mammalian AMP protein kinase of the invention, and convenient fragments thereof, may also be used to raise antibodies. Such antibodies have a number of uses which will be evident to the molecular biologist of ordinary skill. These include (i) monitoring protein expression in native cells and clones which express recombinant AMP protein kinase, (ii) the development of assays to measure kinase-kinase and kinase phosphatase and (iii) the precipitation of AMP protein kinase and other proteins which associate with AMP protein kinase leading to identification of these proteins.

We have found that AMPK shows 46% sequence identity to the protein encoded by the yeast SNF 1 gene, the product of which is essential for release from glucose repression. Whilst we do not wish to be bound by theoretical considerations, AMPK and SNF1 may form part of a family of protein kinases that respond to metabolites rather than second messengers. We disclose the expression of mammalian AMPK in yeast and structure/function analysis undertaken after in vitro site-directed mutagensis/gene deletion. We also disclose the over-expression of AMPK in yeast and analysis of the effects of increased protein kinase activity on lipid biosynthesis and other cellular processes studied in this lower eukaryote. In addition we disclose the expression of AMPK as a fusion protein in cells of hepatic origin and the identification of substrates and other proteins which interact with AMPK in these cell types, for example using the procedures disclosed by Yang et al in Science, 1992, 257, 680–682.

The invention will now be illustrated but not limited by reference to the following Figures and Examples wherein:

BRIEF DESCRIPTION OF THE DRAWINGS

FIG. 2 illustrates the generation of a unique oligonucleotide probe from the amino acid sequence of peptide EL1 derived from rat AMPK. Primer 1 (SEQ ID NO: 4) and primer 3 (SEQ ID NO: 8) (as described hereinafter) were used in PCR with rat liver cDNA and an aliquot of the reaction products was used as a template for a second round of amplification using primers 2 (SEQ ID NO: 6) and 4 (SEQ ID NO: 10) to generate the nucleotide sequence encoding peptide ED1 (SEQ ID NO: 30) as described in the Experimental Procedures.

FIG. 6 shows a comparison of AMPK and Yeast SNF1 Protein Sequences. The deduced protein sequences of rat AMPK (top) and SNF1 (bottom) were aligned using the GAP programme on the University of Wisconsin package, with a gap weight of 3.0 and length weight 0.1. Dots indicate gaps introduced to maximise the alignment. Identities are boxed and shaded.

Figure 1A:
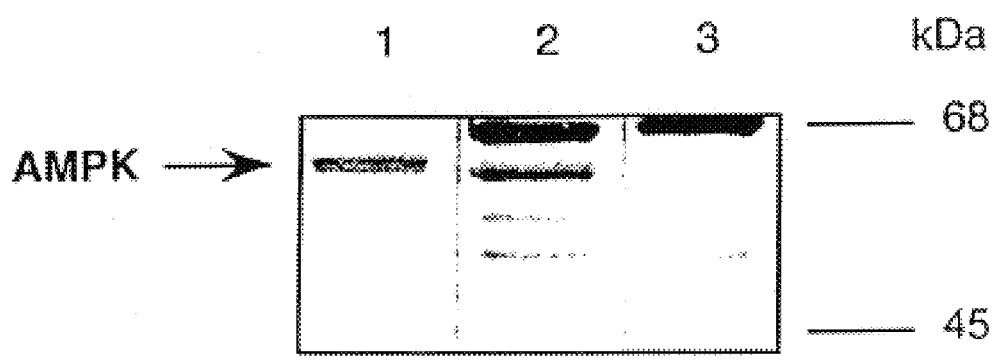
FIG. 1 illustrates the identification of the polypeptide corresponding to AMPK purified from rat liver.
(A) The effect of dephosphorylation on the mobility of AMPK polypeptide as determined by SDS-PAGE: AMPK was purified from rat liver up to and including gel-filtration on Superose 12 as previously described (Carling, et al., Eur. J. Biochem, 1989, 186, 129–136). 10 μg of the preparation was incubated for 30 min at 30° C. either in the absence (Lane 1) or presence (Lane 2) of the catalytic subunit of protein phosphatase 2A. The samples were analysed by SDS-PAGE and protein visualised by straining with Coomassie. Lane 3 shows the protein strain of the phosphatase 2A preparation alone. The positions of molecular weight standards are indicated on the right of the figure.
(B) In Situ phosphorylation of AMPK. 10 μg of AMPK (as in A) was separated by electrophoresis on a denaturing 10% polyacrylamide gel and transferred to PVDF membrane. Proteins on the blot were subjected to an in vitro protein kinase assay using the method of Celenza and Carlson (Mol. Cell. Biol. 1986, 9, 5034–5044). The blot was washed and autoradiographed at –70° C. for 1 hour. The position of molecular weight standards are shown on the right of the autoradiograph.

(B) In an experiment similar to that described for (A), AMPK was incubated with either preimmune serum (40 l) or increasing amounts of antiserum raised against the peptide spanning amino acids 361–374 of AMPK. The total volume of antiserum added was kept constant by the addition of preimmune serum. The immune complex was precipitated with protein A-Sepharose and AMPK activity was determined in both the supernatant fraction and in the resuspended precipitate. Activities are plotted as the percentage of the activity in the supernatant using preimmune serum alone.

(C) Cell lysates from [$^{35}$S] methionine labelled Sf9 cells infected with recombinant AMPK baculovirus were immunoprecipitated as described in (A). The immunoprecipitated proteins were analysed by SDS-PAGE, followed by autoradiography. Lane 1, total cell lystate; lane 2, preimmune serum; lane 3 Ab 278/291; lane 4, Ab361–374; lane 5, Ab 476/489; lane 6, Ab 496/509. Position of molecular weight standards are indicated on the right.

FIG. 8 shows peptide sequence generated from a 63 kd AMP protein kinase by proteolytic and chemical cleavage.

Figure 9B:
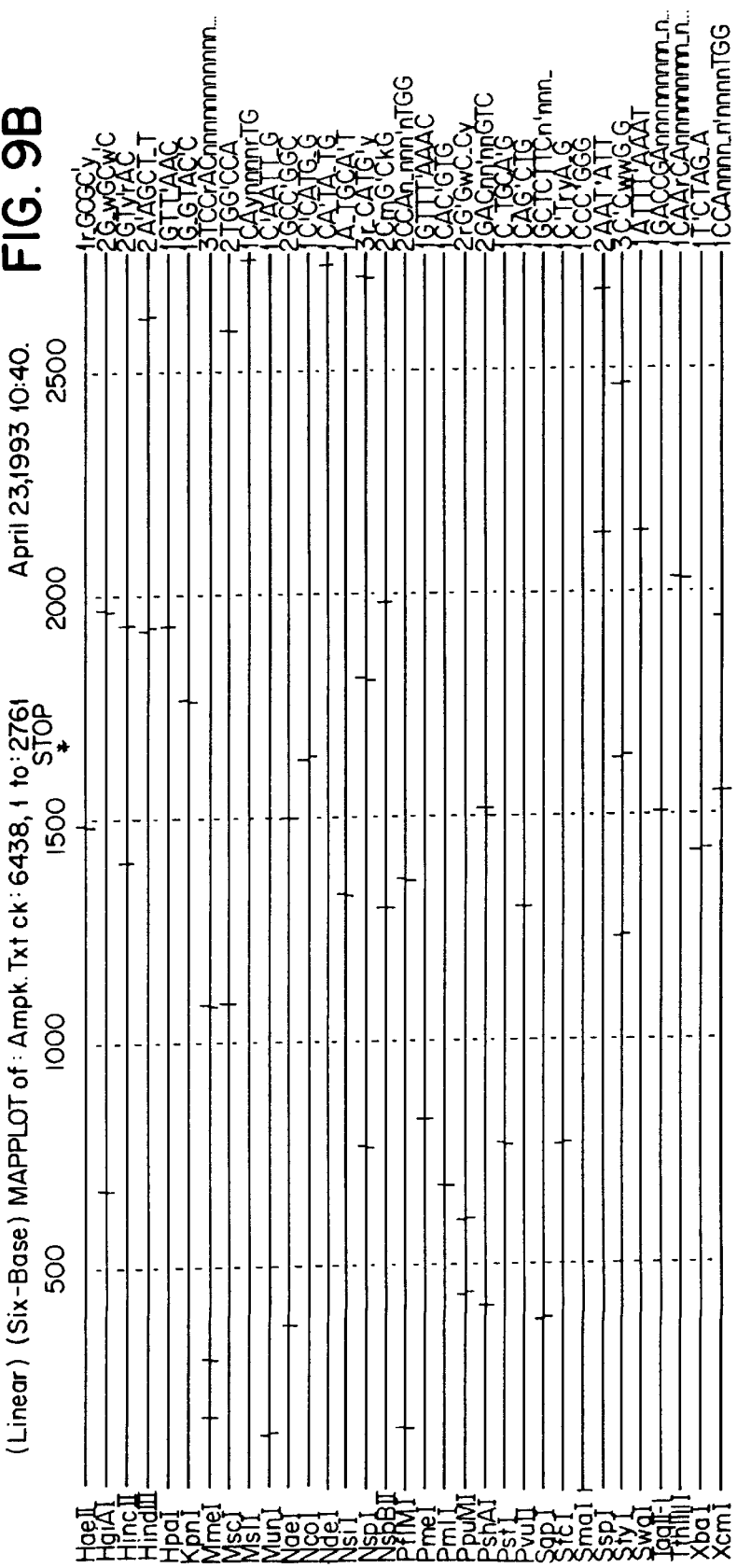

FIG. 9 shows the linear (six base) MAPPLOT restriction map of the cDNA of SEQ ID NO: 24.

FIG. 10 shows amino acid sequence information obtained form peptides derived from AMPK. Residues in brackets are either tentative assignments or assumptions based on the method of cleavage. Residues marked X could not be identified by amino acid sequencing. The amino acid sequences of all the peptides were found in the cDNA clone (FIG. 3A), except for the differences indicated below the peptide sequence.

FIG. 11 shows a comparison of the full-length cDNA coding sequences of cloned rat and human AMP protein kinases.

EXAMPLE 1

Cloning of a CDNA Encoding an AMP-Activated Protein Kinase

Purification of AMP-Activated Kinase

Purification of the AMP protein kinase from rat liver was performed according to the method disclosed by Carling et al (Eur. J. Biochem. 1989, 186, 129–136) as far as the Superose-12 gel filtration step. The resulting partially purified kinase preparation was resolved by SDS-PAGE on 10% polyacrylamide gels (Laemmli, Nature, 1970, 227, 680–685).

Derivation of Peptide Sequences

Three separate preparations of the AMP protein kinase failed to yield N-terminal sequence, which suggested that the intact kinase protein has a blocked N-terminus. In order to obtain internal amino acid sequence, AMP protein kinase was excised from SDS polyacrylamide gels following electrophoresis and cleaved either enzymatically (with S. aureus V8 protease or endoproteinase lys-C) or chemically (cyanogen bromide).

Proteolytic digestion was performed during SDS-PAGE by the method of Cleaveland et al (J. Biol. Chem. 1977, 252, 1102–1106). Following electrophoresis, the peptides were transferred to PVDF membranes, visualised by staining with coomassie and subjected to automated amino acid sequence analysis.

Chemical cleavage was performed by overnight incubation of the gel slice with Cyanogen bromide in 90% formic acid at room temperature. The supernatant was removed and the pellet dried in a Speed-Vac aspirator. The residue was washed twice with water, dried and resuspended in SDS-gel loading buffer (Davison et al, J. Gen. Virology, 1992, 73, 2709–2713). Peptides were resolved by SDS-PAGE and subjected to sequence analysis on an Applied Biosystems 475 sequencer. The above proteolytic cleavage gave the following peptide sequences:

```
Peptide PK0:  (SEQ ID NO: 1)
Peptide PK1:  (SEQ ID NO: 2)
Peptide PK2:  (SEQ ID NO: 3)
```

X=unknown residue ()=uncertainty of residue

At a later stage, the 63 kd protein (20 μg) was also cleaved with cyanogen bromide and additional peptide sequences were generated (see Table 1). For example, a fragment of approximate size 14 K was sequenced to give the sequence BT1. A second fragment of 7 K was analysed and shown to give more than one amino acid residue at each sequencer cycle. This indicates that more than one polypeptide species was present. However, given the deduced cDNA sequence, the peptide sequence data generated was consistent with peptides BT1 and BT2 being present. A 12 K fragment was sequenced and gave the data corresponding to BT3. Finally, an 8 K fragment was sequenced and gave the data corresponding to BT4. Peptides BT1–BT4 are all preceeded by a methionine residue in the deduced sequence, which is consistent with cleavage by cyanogen bromide. The sequences of the derived peptide were confirmed by comparison to the cloned cDNA (see SEQ ID NO: 24 and below) and were also used to confirm the correct reading frame of the cloned cDNA.

Using the original peptide sequence information from proteolytic digests (see above), we concentrated on peptide PK0 which shared residue similarity to all protein kinase sequenced to date (underlined; see Hanks et al, Science, 1988, 241, 42–52. In order to provide unambiguous DNA sequence encoding peptide PK0, messenger RNA was isolated from rat liver and converted to cDNA using a pre-amplification kit (Gibco-BRL, according to the manufacturer's instructions).

A number of degenerate oligonucleotides were synthesised based on the sequence of PK0. These were as follows (A. A. sequence=amino acid sequence):

```
PKAOligonucleotide

5'-NNN CCN GA(A/G) AA(T/C) GTN (C/T)TN (C/T/A)(C/T)N GA-3'      (SEQ ID NO: 4)

A.A.    X    P    E      N       V    L       T/L          D        (SEQ ID NO: 5)
sequence PKBOligonucleotide

5'-CCN GA(A/G) AA(T/C) GTN (C/T)TN (C/T/A)(C/T)N GA(T/C) G-3'   (SEQ ID NO: 3)

A.A.    P    E    N    V    L       T/L          D    A              (SEQ ID NO: 7)
sequence PKDOligonucleotide

5'-CAT (G/A)TT N(G/C)(A/T) NA(G/A) NCC (G/A)AA (A/G)TC NGC-3'   (SEQ ID NO: 8)

A.A.    M    N    S          L       G    F       D    A            (SEQ ID NO: 9)
sequence PKCOligonucleotide 5'-(G/A)TT N(G/C)(A/T) NA(G/A) NCC (G/A)AA (A/G)TC NGC (G/A)TC-3'   (SEQ ID NO: 10)

A.A.    N    S          L       G    F       D    A    D            (SEQ ID NO: 11)
sequence
```

DNA Sequence Key
PKA=potential DNA sequence of N-terminal region of PK0 in sense orientation
PKB=as PKA but nested at the 3'-end
PKD=potential DNA sequence of C-terminal region of PK0 in antisense orientation
PKC=as PKD but nested at the 3'-end.
N=all combinations of nucleotides
()=nucleotide combinations depending on codon degeneracy
Amino acid key is as indicated previously.

Both a 1:10 (Reaction A) and a 1:100 (Reaction B) dilution of the cDNA synthesied earlier were made and 1 µl of this cDNA was used as template for PCR. The other compounds in the reaction were 10× Taq Polymerase buffer (Promega, UK), deoxynucleotide triphosphates (dNTPs) at a final concentration of 100 µM, Primer PKA and PKD at final concentrations of 50 pmoles. The reaction volume was adjusted to 50 ul with water and overlaid with mineral oil (Sigma). The template was denatured by heating to 95° C. for 5 minutes (using the Thermal cycler—M J Research) and the sample held at 70° C. prior to the addition of 1 unit of Taq Polymerase (Promega). The reaction constituents were then subjected to the following cycling regime: 94° C. 2 mins, 55° C. 2 mins, 72° C. 2 mins for 40 cycles.

The products were analysed on an ethidium bromide stained agarose gel and a visual inspection carried out in order to detect the predicted product size of approximately 70 base-pairs (based on the prediction form the PK0 peptide size). This product was not visible.

Accordingly, 1 µl from Reaction A (above) and 1 µl from Reaction B, together with 1 µl of a 1:100 dilution of these reactions was transferred to a new set of reactions using the conditions as outlined above but carrying out the PCR using the nested set of primers PKB and PKC. The PCR products were once again analysed using ethidium bromide stained agarose gels. A product of the expected size was visible in all samples but strongest using cDNA from the original 1:100 dilution (Reaction B). Template from this dilution was then subsequently used to generate quantitative amounts of PCR product which was eluted from the gel using standard procedures (Sambrook, J., Fritsch, E. F. and Maniatis, T. (1989) Molecular Cloning; A laboratory manual (2nd edition).

The PCR product was "polished" (blunt-ended) using T4 polymerase using published procedures (Sambrook et al, cp cit) and cloned into SmaI-digested pBluescript (Stratagene) using T4 ligase according to the manufacturers instructions (Pharmacia). The ligation products were plated out onto the appropriate agar media with antibiotics & chromogenic substrate (Stratagene). Putative recombinants (white) were identified and plasmid DNAs isolated from seventy two such clones according to a procedure described by Del Sal et al (Biotechniques, 1989, 7, 514–519). The plasmid DNAs were digested with EcoRI and XbaI (which flank the SmaI cloning site) and digested DNAs analysed using agarose gels. In total, sixteen clones revealed the expected product size of approximately 150 base pairs (cDNA sequence together with vector sequence internal to the enzymes used in the digestion).

Plasmid DNA from the sixteen clones was denatured according to the method of Hsaio (Nucl. Acid. Res., 1991, 19, 2787) and sequenced with a pBluescript vector primer using a T7 DNA sequencing kit (Pharmacia, instructions followed). Of the sixteen clones, eight had the same sequence internal to the nested primers used. This sequence was:

```
GCC CAG ATG AAT GCT AAG    (SEQ ID NO: 12)

Ala Pro Met Asn Ala Lys    (SEQ ID NO: 13)
```

The above sequence clarified two points pertaining to the original PK0 peptide. Firstly, the ambiguity surrounding (Q/P) was resolved to show that the residue is Proline (P). Secondly, the X residue was shown to be Lysine (K). Based on the above nucleotide sequence, the following oligonucleotide was sythesised: (SEQ ID NO: 14) GAC GCC CAG ATG AAT GCT AAG, end-labelled with T4 kinase (Sambrook et al, op cit) and used as a probe to screen a rat liver cDNA library (Stratagene). The conditions of hybridisation were 30 ng radiolabelled probe (radiolabelled using an oligo-labelling kit from Pharmacia; ~$10^9$ cpm/ug; $10^6$ cpm/ml) in 5×SSPE, 100 ug/ml sonicated and denatured salmon sperm DNA, 2×denhardts, 0.1% SDS at 50° C. for 4 hours. Filters were washed with 5×SSC, 0.1% SCS at room temperature for 2 hours followed by 5×SSC/0.1% SDS at 50° C. for 10 minutes and autoradiography for 18 h at −70° C. with intensifying screens for references refer to Sambrook et al, 1989).

A total of $1.5 \times 10^6$ plaques were screened and eleven hybridising clones were isolated. Plasmids were recovered from the phage by the procedure of in vivo excision as outlined in the manufacturers instructions. Analysis of the inserts by restriction endonuclease mapping revealed that the clones could be divided into two groups: clones PK-1 ($_{1-8}$; 8 clones) contained an insert of 2.6 kb, whilst clones PK-2 ($_{9-11}$; 3 clones) had an insert of −2.7 kb. The inserts from both sets of clones were sequenced on both strands using vector derived primers and subsequently AMP protein kinase cDNA derived primers.

Sequence analysis of PK-1 clones revealed an open reading frame coding for 528 amino acids which included all the peptides listed in FIG. 8. However, sequence PK-1 did not contain an in-frame initiating methionine residue, nor did it include amino acid sequences resembling subdomain I found in all other protein kinases (Hanks et al, op cit). It was therefore concluded that this clone was incomplete at its 5'-end. Clone PK-2 was sequenced and found to be almost identical to the sequence of clone PK-1 but with additional sequence at the 5'-end. The additional 5'-end sequence coded for an in-frame methionine residue in a very good context for translation initiation (Kozek et al, J. Biol. Chem., 1991, 266, 19867–19870). This was followed by protein sequence highly homologous to protein kinase subdomain I (Hanks et al, op cit). However, further analysis of this clone revealed a 142 base pair deletion immediately downstream of the sequence coding for subdomain I as compared to clone PK-1. The deletion leads to the generation of a premature stop codon in the AMP protein kinase protein sequence, resulting in a truncated peptide of only 34 amino acids. The possible significance of this deletion is unclear.

In order to construct a full length cDNA containing the entire coding sequence of AMP protein kinase, rat liver cDNA was amplified using primers based on clones PK-1 and PK-2 (forward primer) (SEQ ID NO: 15) 5'-GCCGAACATGGCTGAGAAG-3'; reverse primer: (SEQ ID NO: 16) TCTTAGCATTCATCTGGGC-3'). A product of the expected size was visible on agarose gels and was eluted from the gel and cloned into pBluescript by the procedure of T:A cloning (Marchuk et al, Nucl. Acids. Res. 1991, 19, 1154). Following sequencing of the cDNA to verify its orientation and integrity, the recombinant pBluescript was digested with NotI and BglII to release a fragment of 160 base pairs. This fragment was purified and ligated onto clone PK-1 that has also been digested with BglII and NotI. The resulting clone (pBS-APK) was identified by restriction mapping of plasmid minipreps and sequenced once again to show clone integrity. This plasmid contains the full length sequence of AMP protein kinase.

INTRODUCTION TO EXAMPLES 2–7

AMP-activated protein kinase (AMPK) plays a central role in the regulation of mammalian lipid metabolism (Carling et al., 1987, 1989a, 1991: Hardie et al., 1989). AMPK phosphorylates and inactivates acetyl-CoA carboxylase, the enzyme catalysing the first committed step in fatty acid synthesis. AMPK also phosphorylates and inactivates 3-hydroxy-3-methylglutaryl (HMG)-CoA reductase, a key regulatory enzyme in the sythesis of chlo- resterol and other isoprenoid compounds. Further studies have shown that AMPK phosphorylates hormone-sensitive lipase in vitro (Garton et al.), 1989. AMPK, therefore, has the potential to regulate both the synthesis and breakdown of triglycerides and cholesterol esters.

The sites phosphorylated within acetyl-CoA carboxylase by AMPK have been identified directly by amino acid sequencing (Munday et al. 1988; Davies et al., 1990) as serine-79, serine-1200 and serine-1215 compared to the predicted sequence deduced from rat cDNA clones (Lopez Casillas et al., 1988. Phosphorylation of these sites has been observed in both isolated adipocytes and in vivo (Haystead et al., 1990). Davies et al., 1992). Recently, it has been shown that phosphorylation of serine-79 can account for most, if not all, of the inactivation of acetyl-CoA carboxylase observed in vitro (Davies et al., 1990). Furthermore, the degree of phosphorylation of serine-79 was shown to increase in response to glucagon treatment of isolated hepatocytes (Sim and Hardie, 1988) and glucagon or adrenaline treatment of adipocytes (Haystead et al., 1990), in parallel with a decrease in the activity of acetyl-CoA carboxylase. These results, taken together with the fact that no other protein kinases tested to date have been shown to phosphorylate serine-79, argue strongly in favour of a role for AMPK in the control of fatty acid sythesis.

In contrast to acetyl-CoA carboxylase, the role of phosphorylation of HGM-CoA reductase has been much more controversial. HGM-CoA reductase is subject to a number of forms of regulation, and in fact has been cited as one of the most regulated enzymes in nature (Brown and Goldstein, 1990). Although phosphorylation and inactivation of HMG-CoA reductase in vitro was demonstrated over 15 ago (Nordstrom et al., 1977; Ingebritsen et al., 1978, 1979; Beg et al., 1980) the importance of this form of regulation has, to a large extent been ignored. This was due to the fact that it appeared that the enzyme always existed in a highly phosphorylated state, despite being able to measure changes in the rates of hepatic cholesterol synthesis (Nordstrom et al., 1977; Brown et al., 1979). However, recent developments in the isolation of HMG-CoA reductase, notably the use of cold-clamping (Easom and Zammit, 1984a), have shown that both phosphorylation and activity of HMG-CoA reductase change acutely in response to diet and hormonal status (Easom and Zammit, 1984b, 1987). The residue phosphorylated within HMG-CoA reductase by AMPK has been identified by amino acid sequencing of the purified, soluble 53 kDa proteolytic form of the enzyme (Clark and Hardie, 1990a) and corresponds to serine-871 in the hamster sequence (Chin et al., 1984). Although this residue can be phosphorylated by both protein kinase C and $Ca^{2+}$— calmodulin-dependent protein kinase in vitro (Clark and Hardie. 1990b) there is no evidence to suggest that these kinase play a physiological role in the phosphorylation and inactivation of HMG-CoA reductase (Zammit and Caldwell, 1991). However, there is good evidence that, under certain conditions, HMG-CoA reductase in isolated hepatocytes is phosphorylated by AMPK (Gillespie and Hardie, 1992).

In addition to acetyl-CoA carboxylase and HMG-CoA reductase, AMPK phosphorylates hormone-sensitive lipase (Garton et al, 1989) a regulatory enzyme involved in the hydrolysis of triglycerides and cholesterol-esthers (Cooke et al., 1982). Hormone-sensitive lipase purified from bovine adipose tissue has been used to identify the residue phosphorylated by AMPK (Garton et al., 1989). This was found to correspond to serine-565 as predicted by the sequence deduced from rat cDNA clones (Holm, et al., 1988). Phosphorylation of this site has been observed in vivo (Garton et al., 1988), and may prevent the activation of hormone-sensitive kipase by cyclic-AMP-dependent protein kinase (Garton et al., 1989; Garton and Yeaman, 1990). As well as being involved in the regulation of lipid metabolised enzymes, there in some evidence that AMPK may play a wide role in cellular processes. AMPK phosphorylates glycogen synthase and phosphorylase kinase in vivo (Carling and Hardie, 1989b) at sites known to be phosphorylated in vivo (Poulter et al, 1991; Heilmeyer, 1991). However, in the case of glycogen synthase, the site phosphorylated to AMPK can also be phosphorylated by a number of other protein kinases, including cyclic-AMP-dependent protein kinase, and the physiological significance of phosphorylation of this enzyme by AMPK has not been fully addressed.

AMPK has been purified over 3000-fold from rat liver and its biochemical properties have been examined (Carling et al, 1989a). As its name indicates AMPK is activated by AMP (approximately 5-fold by concentrations of AMP in the micromolar range), and this activation appears to be extremely specific for AMP since no other nucleotides or nucleotide analogues that were tested had any significant effect on the activity of the enzyme (Carling et al., 1989a). A second form of regulation of AMPK is by reversible phosphorylation. AMPK can be inactivated by in vitro by treatment with purified protein phosphatases (Carling et al., 1987). Demonstration of phosphorylation and activation of AMPK has proved difficult, but partially purified preparations of the kinase can be reactivated in the presence of MgATP (Carling et al., 1989). This MgATP-dependent reactivation was not due to an autophosphorylation reaction, since more highly purified preparations of the kinase could not be reactivated in the presence of MgATP. Although cyclic-AMP has been shown to be essential in the signal transduction pathway whereby glucagon and adrenaline exert their effects on fatty acid synthesis by the phosphorylation of acetyl-CoA carboxylase (Haystead et al., 1990) cyclic-AMP-dependent protein kinase has no effect on the activity of AMPK in vitro (Davies et al., 1989). Little progress has been made on the purification and characterisation of the protein kinase responsible for the phosphorylation and activation of AMPK, although it clearly represents an important control point in the regulation of lipid metabolism.

We now describe the purification and amino acid sequencing of AMPK together with the isolation of AMPK, cDNA clones. Antibodies directed against synthetic peptides derived from the predicted sequence of the kinase specifically immunoprecipitate the activity of AMPK from rat liver. The sequence of AMPK shows 47% identity to the protein encoded by the yeast SNF 1 gene (sucrose non fermenting). The protein product of the SNF 1 gene is a protein kinase which has been shown to be essential for the release form glucose repression (Celenza and Carlson, 1986). We propose that AMPK and SNF 1 may form part of a larger family of protein kinases that respond to the levels of intracellular metabolites rather than the more classical second messengers, and whose functions include, but may not be limited to, responding to metabolic stress.

EXAMPLE 2

Purification and Amino Acid Sequencing of AMPK

Figure 1B:
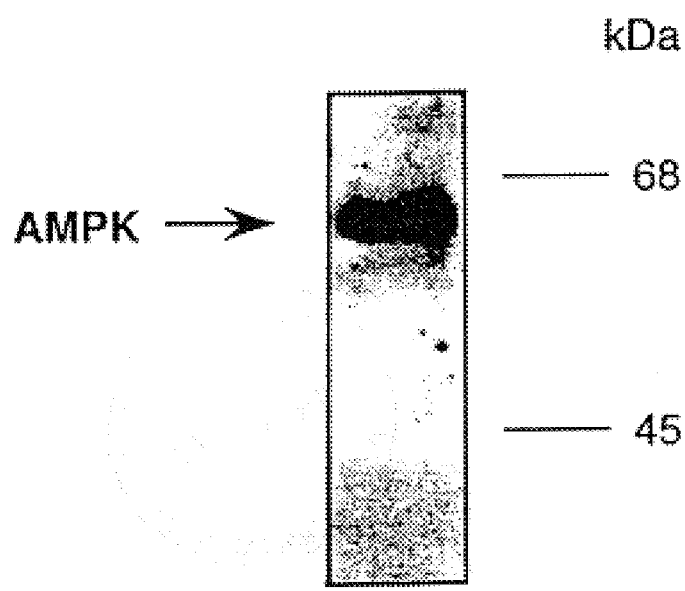

The polypeptide corresponding to AMPK has been identified previously by SDS-PAGE following covalent labelling of the enzyme with the ATP-analogue, fluorosulphonylbenzoyladenosine (FSBA) (Carling et al., 1989a). A single, labelled polypeptide was observed with an apparent molecular mass of 63 kDa. We have confirmed that this polypeptide corresponds to AMPK and have isolated cDNA clones encoding the kinase. AMPK was purified approximately 3000-fold from rat liver and the polypeptide corresponding to the kinase purified by SDS-PAGE. The identity of this polypeptide was confirmed by the following criteria:

1) Reaction of the kinase preparation with $^{14}$-C-FSBA resulted in specific labelling of a single 63 kDa polypeptide (Carling et al., 1989a, and data not shown);

2) In some preparations of the kinase the 63 kDa polypeptide migrated as a distinct doublet following SDS-PAGE (FIG. 1A: lane 1). It is likely that this is due to differences in the phosphorylation state of the enzyme, since it is known that the AMPK is regulated by phosphorylation. Treatment of AMPK with the catalytic subunit of protein phosphatase 2A, which caused almost complete inactivation of AMPK, resulted in a shift in the migration of the upper band of the doublet to that of the lower band (FIG. 1A; lane 2). No changes in the migration of any other bands in the preparation were observed;

3) The same 63 kDa polypeptide was labelled following an in situ phosphorylation assay utilising [r-$^{32}$P] (Celenza and Carlson, 1986) shown in FIG. 1B;

4) Amino acid sequence derived from the 63 kDa polypeptide showed extensive homology to protein kinase subdomains (FIG. 10).

On three separate occasions, from two different preparations of AMPK, no sequence was obtained form the intact polypeptide, suggesting that the kinase had a blocked N-terminus. However, several peptides derived by cleavage of AMPK did yield amino acid sequence and these are shown in FIG. 10. Analysis of the Swiss-Prot data base revealed that the sequence of EL1 (and SV1, which is derived from EL1) was similar to sequences found within other protein kinases spanning subdomain VIb-VII (Hanks and Quinn, 1991) and that CB1 was homologous to protein kinase subdomain V.

EXAMPLE 3

Isolation of AMPK CDNA Clones

We are able to obtain a unique DNA sequence encoding a portion of AMPK by PCR using rat liver cDNA and degenerate oligonucleotide primers corresponding to potential sequences encoding peptide EL1: FIG. 2). Based on the sequence of the amplified product, a unique oligonucleotide was synthesised and used to screen a rat liver cDNA library. Eleven positive plaques were isolated which could be divided into two groups: clones PK-1 and PK-2. Sequence analysis of clone PK-1 revealed a potential open reading frame coding for 528 amino acids which included all of the peptide sequences listed in FIG. 10. However, the deduced translated sequence did not contain an in frame initiating methionine residue, nor did it include amino acid sequences resembling subdomain I found in all other protein kinases sequenced to date (Hanks and Quinn, 1991). It was therefore concluded that this clone was incomplete at its 5' end. Clone PK-2 was sequenced and was found to be almost identical to the sequence of clone PK-1, and to include additional sequence at the 5' end. The deduced translation of the additional 5' sequence resulted in an in-frame methionine residue which was in a very good context for translation initiation (Kozak, 1987) and was followed by protein sequence highly homologous to protein kinase subdomain I (Hanks and Quinn. 1991). However, further analysis of PK-2 revealed that it had a 142 base pair deletion, as compared to clone PK-1, immediately downstream of the sequence coding for subdomain I.

Figure 3B:
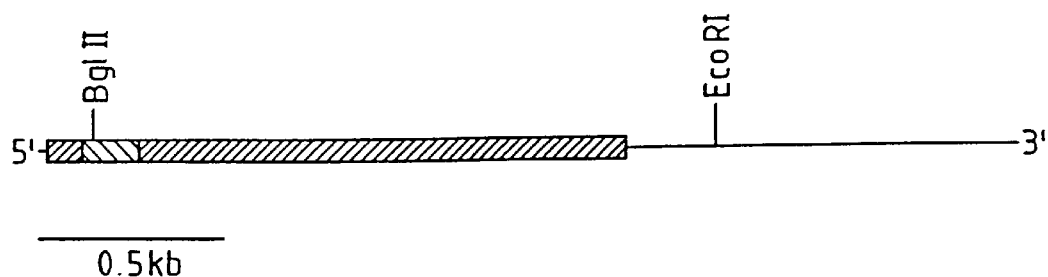
FIG. 3 shows the nucleotide (SEQ ID NO: 38) and deduced protein (SEQ ID NO: 40) sequences of rat AMPK (A) Nucleotides are numbered on the left and amino acids on the right. Peptide sequences derived from purified AMPK are underlined. They putative initiation codon and the stop codon are shown in bold type. The nucleotides in the 142 bp deletion (nucleotides 102–216) are shown in italics and the boundaries of the deletion marked by vertical arrows.
(B) Schematic diagram of part of the mRNA for AMPK. The coding region is shown boxed and the 5' and 3' untranslated regions are indicated by the solid lines. The position of the 142 bp deletion is indicated by cross-hatched markings. The BglII and EcoRI restriction endonuclease sites used in constructing various vectors are also shown. The scale is indicated by the solid bar.

An overlapping clone (pBS-APK) containing the cDNA encoding the entire deduced protein sequence of AMPK was made from PK-1 and PK-2. The nucleotide sequence, together with the deduced protein translation, of the composite clone is shown in FIG. 3A. A schematic representation of the clone, highlighting the deleted sequence is shown in FIG. 3B. The first ATG codon of the open reading frame occurs in a good context for translation initiation (Kozak, 1987), although no stop codons were found upstream. We believe that this is the initiating methionine since the protein encoded by the cDNA has a mass of 62,250 daltons which is almost identical to that observed for the enzyme isolated from rat liver. The open reading frame is followed by 1 kb of untranslated sequence, but there is no obvious polyadenylation signal or poly A tail, which, taken in conjunction with the results of the Northern analysis, indicate that the clone is incomplete at the 3' end.

EXAMPLE 4

Alternative Splicing of AMPK mRNA

Figures 4A, 4B:
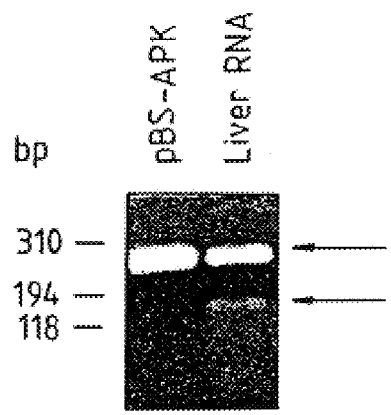
FIG. 4 illustrates the identification of two transcripts for AMPK mRNA.
(A) Rat liver cDNA was synthesised from total RNA using random hexamers and used as a template for PCR using AMPK specific primers (see Materials and Method section). In a separate reaction, pBS-APK was used as a control. The products of the reaction were analysed by electrophoresis on a 1.2% agarose gel and visualised by staining with ethidium bromide. The position of DNA standards are indicated.
(B) The nucleotide and predicted protein sequences of the AMPK transcript having a 142 bp deletion is shown beginning at the presumed initiating methionine and extending to the stop codon. Amino acid residues encoded by the sequence downstream of the deletion are shown in italics and the stop codon indicated by an asterix.

In order to examine the nature of the 142 bp deletion from PK-2 in more detail, total RNA isolated from rat liver was reverse transcribed and the cDNA amplified by PCR (RT-PCR) using a sense oligonucleotide near the 5' end of the cDNA (nucleotides 40–56, 5' GAAGATCGGACACTACG 3') (SEQ ID NO: 17) and an antisense oligonucleotide downstream of the deleted sequence (nucleotides 286–303, 5' CCRCCAGACACATATTTCC 3') (SEQ ID NO: 18). Two products, which differed by 142 bp, were identified (FIG. 4A). These two products were cloned into Bluescript and sequenced revealing the shorter product to have the same deletion that was found in the original PK-2 clones. These results indicate the presence of two mRNA transcripts for AMPK, which have been identified in all tissues examined. We have isolated genomic clones for AMPK which span this region and have found that the deleted sequence corresponds to a single exon. The 142 bp deletion leads to the generation of a premature stop codon in the deduced AMPK protein sequence which would result in a truncated peptide of only 34 amino acids (FIG. 4B). Initiation at the next downstream methionine in AMPK would produce a protein of approximately 52 kDa.

EXAMPLE 5

Northern and Southern Analyses

Figure 5A:
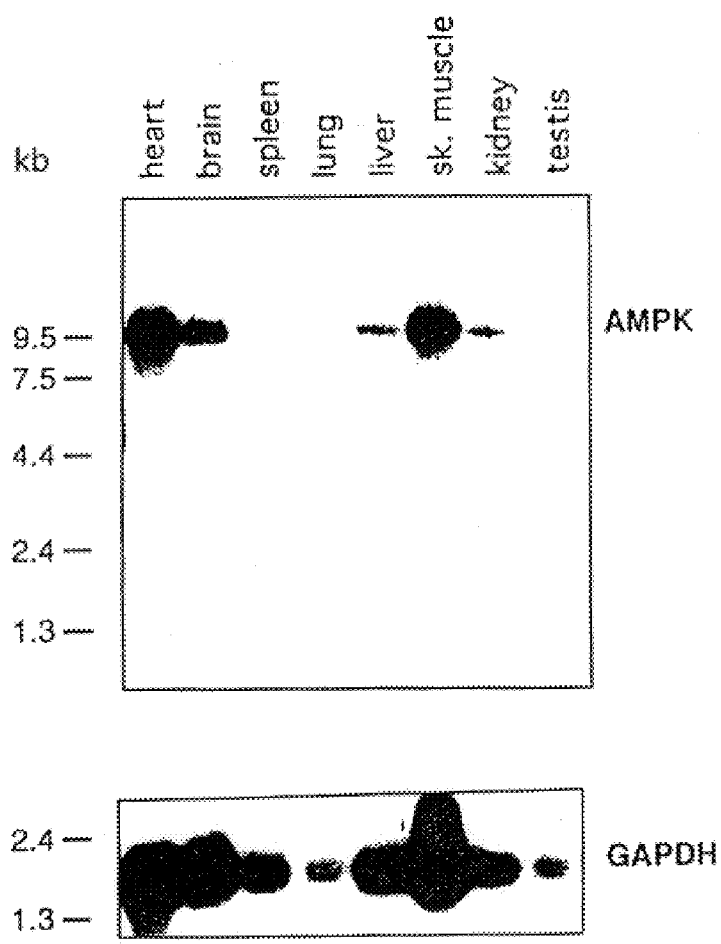
FIG. 5 shows Northern and Southern Analyses.
(A) Northern Analysis
Approximately 2 μg of mRNA from the indicated tissues were separated on a 1.2% agarose gel under denaturing conditions, transferred to a charge modified nylon membrane and probed with a 1.9 kb cDNA fragment of AMPK. The blot was washed under stringent conditions (0.1×SSC, 0.1% SDS, 65° C.) and exposed for 5 days at –70° C. The same blot was stripped and re-probed with a 1 kb fragment of rat glyceraldehyde 3-phosphate dehydrogenase (GAPDH). Positions of RNA standards (kb) are indicated.
(B) Southern Analysis
Approximately 10 μg of rat genomic DNA was digested with the restriction endonucleases shown, separated by electrophoresis on a 1% agarose gel, transferred to a nylon membrane and probed with the entire insert form pBS-APK. The blot was washed under stringent conditions (0.1×SSC, 0.1% SDS, 65° C.) and exposed for 2 weeks at –70° C.
Figure 5B:
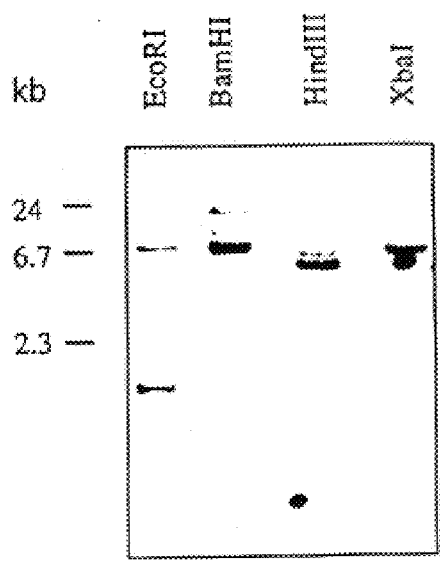

Northern blot analysis of mRNA isolated from a number of rat tissues and probed with part of the AMPK cDNA is shown in FIG. 5A. A single transcript of approximately 9.5 kb is observed in all of the tissues except spleen and testis. The relatively large size of the transcript indicates that the AMPK mRNA contains a long 3' and/or 5' untranslated region, and makes it unlikely that a deletion of 142 bp would be detected by this method. The highest levels of transcript were found in skeletal and cardiac muscle, with only a modest level detectable in the liver. Although there may be differences in the amount of mRNA loaded (as judged by the level of GAPDH message) this could not fully account for the differences in the level of AMPK mRNA we observed. We have quantitated the level of expression of AMPK message in a number of tissues by competitive PCT (Gilliland et al., 1990) and these results confirm the Northern data. Previously, the tissue distribution of AMPK indicated that the highest levels of activity were present in the liver, with almost undetectable levels of activity in skeletal muscle (Davies et al., 1989). Southern blot analysis of rat genomic DNA probed with the entire insert of pBS-APK indicates that AMPK is a single copy gene (FIG. 5B).

DISCUSSION (EXAMPLES 4–5)

We have found that the AMPK gene is expressed in a wide variety of rat tissues. By Northern analysis a single band of approximately 9.5 kb was identified in all of the tissues tested, except spleen and testes. RT-PCT revealed two AMPK transcripts which differed by 142 nt. It is unlikely that a difference of 142 nt in such a large transcript would be resolved by Northern blotting. The two mRNA species are the result in differential splicing of a single exon. The full-length mRNA, in which the 142 bp exon is expressed, encodes AMPK as purified from rat liver. Deletion of the 142 bp exon leads to the generation of a premature stop codon which would result in a truncated peptide of only 34 amino acids. At present, there is no evidence for the existence of such a translation product. This exon is spliced out in a surprisingly high number of AMPK gene products. In most tissues, as much as 40–60% of all AMPK mRNA lacks this exon. Potentially, splicing could represent a powerful mechanism in the regulation of AMPK expression. The observation that splicing of AMPK mRNA occurs to a much lesser extent in skeletal and cardiac muscle than in other tissues would argue in favour of such a regulatory function, and at least suggest that the degree of splicing is tissue-dependent. However, the extent of splicing did not vary markedly in liver during a time-course of starvation and refeeding (data not shown), although AMPK activity has been reported to change 2–3 fold under these conditions. Therefore, the physiological role of this splicing remains unclear.

The abundance of AMPK mRNA in skeletal muscle was determined to be 5-fold higher than in liver. Moreover, only 15% of the message in skeletal muscle lacked the 142 bp exon compared to 40% in liver. Therefore, the transcript encoding functional AMPK is at least 7-fold higher in muscle than in any of the other tissues. In accordance with this, we have detected relatively high levels of AMPK protein in muscle by Western blotting with specific anti-AMPK antibodies. These observations contrast sharply to enzyme activity measurements, which show very little activity in skeletal muscle. Our results imply that muscle AMPK has a low specific enzyme activity compared to the kinase isolated from the liver. AMPK is phosphorylated and activated by a distinct protein kinase in a reaction which is markedly stimulated by AMP. Previously, it has been shown that the high activity of AMPK isolated from rat liver is a consequence of the increased concentration of AMP, presumably caused by hypoxia during dissection of the tissue. In this the same conditions were employed for the isolation of AMPK from skeletal muscle as from liver, so that similar post-mortem effects would be expected in both preparations. Nevertheless, the muscle enzyme appears to be in a different phosphorylated state than the liver enzyme, suggesting that its low specific activity may be due to lack of phosphorylation at the activatory site(s). Whether this reflects the state of the kinase in vivo, or in an artefact of the isolation from muscle, remains to be established. It should be noted that we used resting muscle for these studies; possible activation of AMPK by AMP only occurs after a period of sustained muscle contraction.

AMPK is thought to play an important physiological role in the regulation of acetyl-CoA carboxylase and HGM-CoA reductase, the rate-limiting enzymes in fatty acid and cholesterol synthesis, respectively. In accordance with this, both AMPK mRNA and activity are present in tissues such as liver, mammary gland, lung and brain, which are active in lipid biosynthesis. However, the high level of AMPK expression in skeletal and cardiac muscle, as well as the relatively low level of expression in adipose tissue, may indicate additional functions for this protein kinase. This is further supported by our observation that the tissue-dependent expression of the mRNA encoding ACC, which is shown to be a substrate for AMPK in vivo, is inversely correlated with expression of functional AMPK mRNA.

Although we have been unable to demonstrate appreciable AMPK activity in skeletal muscle, there are a number of possible substrates for the kinase in this tissue. Glycogen synthase and phosphorylase kinase purified from rabbit skeletal muscle have both been shown to be phosphorylate by AMPK in vitro. An increased energy demand during muscle contraction may lead to an increase in AMP. Subsequent activation of AMPK could result in phosphorylation and inactivation of glycogen synthase and concomitant mobilisation of glycogen for the regeneration of ATP. Rat skeletal (and cardiac) muscle appear to predominantly express a distinct isoform of acetyl-CoA carboxylase with molecular mass of 280 kDa ($ACC^{280}$). It is not known whether $ACC^{265}$ and $ACC^{280}$ arise from distinct genes, or from a common gene by alternative splicing. cDNA clones encoding the 265 kDa form, but not the 280 kDa form, have been isolated. The 280 kDa isoform has been proposed to play a role in the control of fatty acid oxidation in muscle. Although there is good evidence that it is regulated by phosphorylation, to date a role for AMPK had not been demonstrated. However, if $ACC^{280}$ is phosphorylated and inactivated by AMPK, then activation of AMPK during increased muscle contraction would lead to a decrease in malonyl-CoA concentration. Malonyl-CoA is a potent inhibitor of carnitine palmitoyltranserase I, a key regulatory enzyme in the transport of fatty acids into the mitochondria. Inhibition of $ACC^{280}$ by AMPK would therefore lead to an increase in the rate of fatty acid oxidation, and hence ATP production.

EXAMPLE 5

Amino Acid Sequence of AMPK and Homology with Other Protein Kinases

A search of the Swiss-Prot database with the predicted protein sequence of AMPK reveals homology with the catalytic domain of other members of the protein kinase family. Interestingly, however, AMPK shows a very high degree of homology (47% identity) with a protein kinase from *Saccharomyces cerevisiae* termed SNF1, which is involved in carbon catabolite depression (Celenza and Carlson, 1986). The amino acid sequence of AMPK and SNF1 protein kinases are compared in FIG. 6. Sequence identity extends throughout the entire protein sequences, although outside of the catalytic domain (which corresponds to the N-terminal halves of the enzymes) the similarity is less extensive. The polyhistidine tract present at the N-terminus of SNF1 is not present in AMPK. However, mutagensis studies in which 12 of the 13 consecutive histine residues were deleted have shown that this sequence is not necessary for SNF1 function (Celenza and Carlson, 1989). A cDNA clone encoding a putative protein kinase has recently been isolated from rye (RKIN1), and the predicted amino acid sequence of this clone shares extensive homology (46% identity) with SNF1 (Alderson et al., 1991) and AMPK (data not shown). The predicted amino acid sequence of AMPK contains a number of serine and threonine residues that lie within good consensus sequences of phosphorylation by known serine/threonine protein kinases. In addition, AMPK contains several potential phosphorylation residues just N-terminal to the conserved Ala—Pro—Glu (APE) motif. Phosphorylation of residues in this region has been shown to be important for the regulation of other protein kinases (Sutherland et al., 1993).

In *Saccharomyces cerevisiae* SNF1 protein kinase activity is essential for release of genes from glucose repression. As already details we have obtained cDNA clones encoding an AMP-activated protein kinase (AMPK) that has been shown to be involved in the regulation of both fatty acid and cholesterol metabolism. The amino acid sequences of SNF1 and AMPK are 46% identical. We investigated whether SNF1 and AMPK shared any functional similarity in addition to their primary sequence homology. We used a synthetic peptide (the "SAMA" peptide which is based on the sequence surrounding one of the sites phosphorylated within acetyl-CoA carboxylase by AMPK as a substrate in a phosphorylation assay in yeast extracts. We were able to detect kinase activity using this assay in wild type yeast extracts which was immunoprecipitated by antibodies raised against either SNF1 or SNF4. The activity of SNF1 has previously been shown to be dependent on the association of SNF4, which is though to be an activatory subunit of SNF1. It is noteworthy that we have identified a 36 kDa polypeptide which co-purifies with rat AMPK by Western blotting using antibodies raised against SNF4 (data not shown). We believe that this polypeptide is likely to be involved in the regulation of mammalian AMPK in the same way that SNF4 regulates SNF1 function in yeast. Protein kinase activity assayed by the phosphorylation of the SAMS peptide was not detectable in a number of mutant yeast strains which have previously been shown to be defective in SNF1 function. These results confirm that the protein kinase activity we were measuring with the SAMS peptide substrate was that of SNF1. Radiosequencing of SAMS peptide (or its parent peptide, SSMS) phosphorylated by SNF1 or AMPK revealed that the same serine residue, corresponding to serine-79 in rat acetyl-CoA carboxylase, was labelled in either case (data not shown). The apparent Km of SAMS peptide for SNF1 (20 $\mu$M) was similar to that of the AMPK (data not shown). However, unlike AMPK we were unable to detect any significant activation of SnF1 by AMP over a range of AMP concentrations (data not shown).

Since SNF1 activity is known to be essential of release from glucose repression we looked at the activity of SNF1 isolated from wild type grown in derepressing conditions (growth in 0.05% glucose). We have found that the activity of SNF1 increases significantly (3 fold) over time during growth under derepressing conditions. This increase in activity was not due to a change in the amount of SNF1 protein, as detected by Western blotting. The time course of SNF1 activation precedes the previously reported time course of invertase activation during derepression, consistent with the idea that SNF1 protein kinase activity is necessary for activating invertase gene expression. The increase in SNF1 activity is due to a covalent modification since the effect survived purification by chromatography on DEAE-Sepharose. We therefore investigated the effect of dephosphorylation on SNF1 activity. Following incubation under conditions that would activate endogenous protein phosphatases present in the yeast extract the activity of SNF1 was dramatically reduced. Furthermore, SNF1 was inactivated by incubation with the purified catalytic subunit of mammalian protein phosphatase 2A. These results indicate that, like AMPK, SNF1 is itself regulated by phosphorylation. Although our results do not discriminate between an autophosphorylation reaction and phosphorylation and activation by a distinct protein kinase, the similarities between SNF1 and AMPK, forms part of a protein kinase cascade, and that SNF1 is phosphorylated and activated during growth under depressing conditions.

Since SNF1 and AMPK share functional homology we examined the activity of acetyl-CoA carboxylase, as substrate for AMPK in vivo, under derepressing conditions in yeast. We have found that the activity of acetyl-CoA carboxylase isolated from yeast growth in 0.05% glucose (derepression) compared to yeast grown in repressing conditions (2% glucose) is decreased approximately 3-fold. The decrease in acetyl-CoA carboxylase activity was due to phosphorylation and inactivation of the enzyme since the effect was observed after purification of acetyl-CoA carboxylase to homogeneity by chromatography on avidin-Sepharose and could be reversed following dephosphorylation using the catalytic subunit of protein phosphatase 2A. The activity of acetyl-CoA carboxylase assayed in crude extracts of snf1 mutant yeast was approximately double that compared to wild type (repressed). Acetyl-CoA carboxylase purified from yeast is phosphorylated and inactivated by SNF1 bound to anti-SNF1 antibody protein A-Sepharose beads in vitro. The simplest interpretation of these results is that SNF1 phosphorylates and inactivates acetyl-CoA carboxylase in vivo. Yeast acetyl-CoA carboxylase does not contain the homologous amino acid sequence corresponding to the inactivatory AMPK phosphorylation site in the rat enzyme (serine-79) although there are a number of potential phosphorylation sites within yeast acetyl-CoA carboxylase.

EXAMPLE 7

Immunoprecipitation of AMPK

Figure 7A:
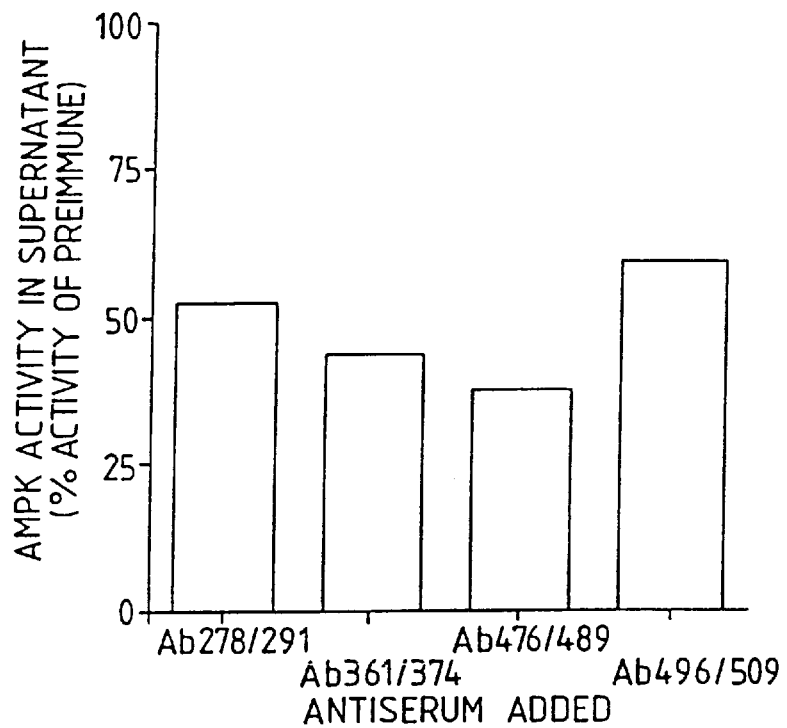
FIG. 7 shows the results of immunoprecipitation of AMPK.
(A) AMPK was purified form rat liver up to the DEAS-Sepharose step (Carling et al., 1989, op cit) and incubated with either preimmune serum (10 μg) or 10 μg of the different antisera raised against four synthetic peptides based on the deduced amino acid sequence of AMPK (cf. Materials and Methods section) (numbering of the antisera refers to the position of the amino acids of the peptides in the full length sequence). After 3 hours protein A-Sepharose was added and the mixture incubated for a further hour at 4° C. The immune complex was then precipitated by centrifugation and AMPK activity remaining in the supernatant fraction determined by the phosphorylation of the 'SAMS' peptide (cf. Materials and Methods section). Activities shown are measured in the presence of 200 μM AMP and are plotted as a percentage of the activity present in the supernatant fraction following precipitation with preimmune serum.
Figure 7B:
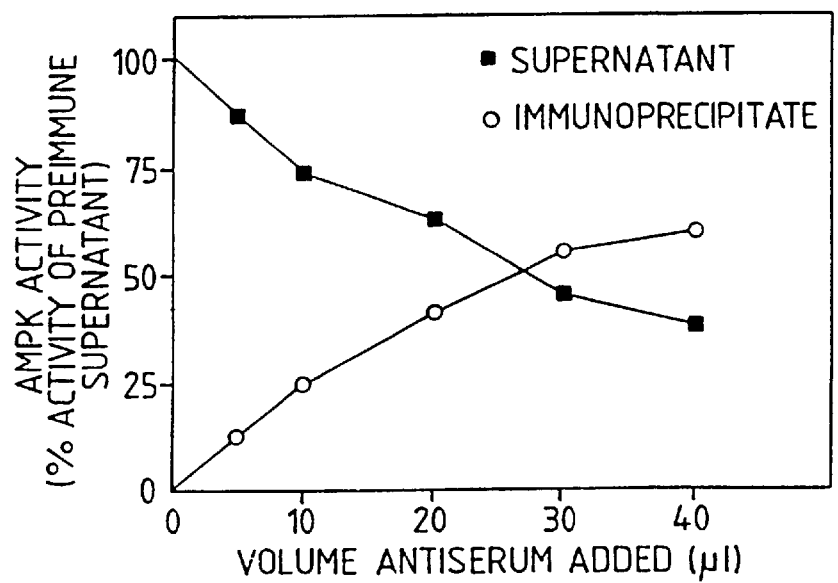

Antibodies raised against four different synthetic peptides based on the deduced protein sequence of AMPK recognised a 63 kDa protein from rat liver by Western blotting (data not shown). Incubation of partially purified AMPK from rat liver (DEAE-Sepharose fraction. Carling et al., 1989a) with the different antisera did not result in any detectable loss in AMPK activity (data not shown). However, following precipitation of the immune complex with protein A-Sepharose there was a loss in activity of AMPK in the supernatant fraction (FIG. 7A). Furthermore, with three of the four antisera. AMPK activity was detected in the immunoprecipitated complex (FIG. 7B and data not shown). By increasing the amount of antiserum added it was possible to increase the amount of AMPK activity that could be precipitated form the supernatant (FIG. 7B). AMPK activity remaining in the supernatant or present in the immune complex precipitate showed identical stimulation by AMP (approximately 3-fold, data not shown). AMPK that had been metabolically labelled by incubation of Sf9 cells infected with recombinant AMPK baculovirus with [$^{35}$S] methionine was specifically immunoprecipitated from the cell lysate by the different anti-peptide antibodies (FIG. 7C). No AMPK activity was detected in any of the immunoprecipitates form Sf9 cells which may be due to the absence of phosphorylation of AMPK in this system (unpublished results).

EXAMPLE 8

Production of Anti-AMPK Antibodies

Based on an antigenicity index (A1) of the cloned rat cDNA sequence (described by Jameson & Wolf, CABIOS, 1988, 4, 181–186), four 15-mer peptides with high A1 values were synthesised. There were peptides based on the predicted amino acid sequences of AMPK for residues 278–291 (SEQ ID NO: 19), 361–374 (SEQ ID NO: 20) 476–489 (SEQ ID NO: 21) 496–509 (SEQ ID NO: 22). They were synthesised and coupled to bovine thyroglobulin (Sigma T1001) via a cystein residue added to the N-terminus of the peptide using M-maleimidobenzoyl-N-hydroxy succinimide ester (Pierce Ltd) (Green et al, Cell, 1982, 28, 477). Male New Zealand white rabbits (3 per conjugate) were immunised and bled as described previously (Forder et al, 1983, 12, 323). Specific antibody binding was demonstrated by binding to respective peptides in a sandwich ELISA (Forder et al, in preparation).

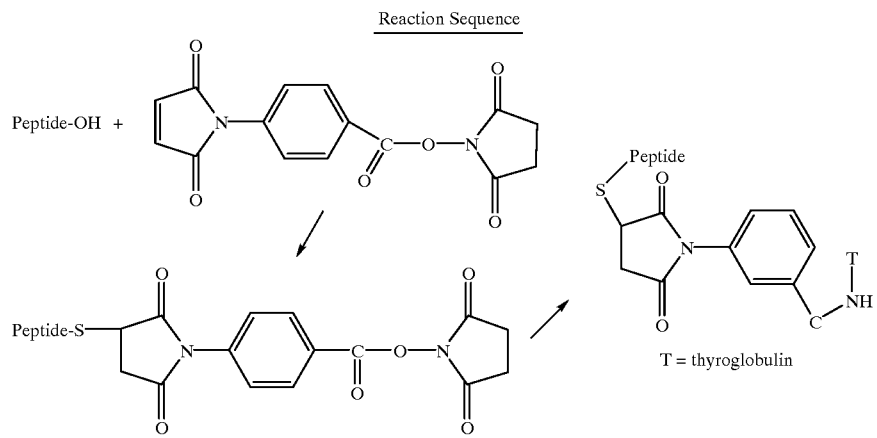

Conjugates were subject to hydrolysis for 24 hours at 130° C. in 6 N/Phenol prior to amino acid analysis. The cystein residue in the peptide is converted to S-succinylcysteine

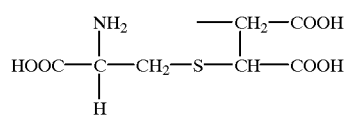

which is a small, fast running identifiable peak on the amino acid analyser. From the number of moles of succinylcysteine formed and knowing the amino acid composition of bovine thyroglobulin, it is possible to determine the molar incorporation of peptide per mole of thyroglobulin. In this instance, less than 10 moles peptide/mol thyroglobulin were not used to immunise animals e.g. residues 476–489=32, 361–374=18, 466–509=24, 278–291=38.

Immunoprecipitation of AMPK

Immunoprecipitation of AMPK was carried out by adding the indicated volume of serum to the kinase preparation followed by incubation at 4° C. for 3–12 h. The volume of antiserum added was kept constant by the addition of preimmune serum were necessary. A 50% (w/w) slurry of protein A-Sepharose was added and the incubation continued for a further hour at 4° C. The mixture was centrifuged at 10,000×g for 10 min. and the supernatant removed and assayed for AMPK activity where necessary. The pellet was washed with 3×100 µl of buffer A containing 1% Triton X-100 and resuspended in this buffer for measuring AMPK activity or in SDS-sample buffer for electrophoretic analysis.

METHODS AND MATERIALS

Purification of AMPK

AMPK was purified from rat liver as fat as the Superose-12 gel filtration step, exactly as described previously (Carling et al., Eur. J. Biochem., 1989, 186, 129–136). Approximately 50 µg of purified AMPK polypeptide (yield determined form Coomassie stained polyacrylamide gels and comparison with known amounts of standards) was obtained from 150 g tissue (10 rats) and used to derive amino acid sequence information. The partially purified kinase preparation was resolved by SDS-PAGE on 10% polyacrylamide gels (Lammlli, Nature, 1970, 227, 680–685).

AMPK Assay

AMPK activity was assayed in vitro by the phosphorylation of a synthetic peptide substrate (SEQ ID NO: 23); the 'SAMS' peptide) as described by Davies et al. (Eur. J. Biochem, 1989, 186, 123–138). Unless indicated otherwise assays were performed at 30+ for 30 mins in the presence of 200 µM AMP using the SAMS peptide at a concentration of 200 µM.

Isolation and Amino Acid Sequencing of AMPK Peptides

The 63 kDa polypeptide identified as AMPK was excised from SDS-polyacrylamide gels following electrophoresis and cleaved either enzymatically (S-aureus V8 protease or endoproteinase lys-C) or chemically (cyanogen bromide). Proteolytic digestion was performed during electrophoresis by the method of Cleveland et al. (J. Biol. Chem., 1977, 252, 1102–1106). Following electrophoresis the peptides were transferred to PVDF membrane, visualised by staining with Coomassie and subjected to automated amino acid sequence analysis. Chemical cleavage was performed by overnight incubation of the gel slice withcyanogen bromide in 90% formic acid at room temperature. The supernatant was removed and dried in a Speed-Vac. The residue was washed twice with water, dried and resuspended in SDS-gel loading buffer. Peptides were resolved by SDS-PAGE using a tricine buffer system (Schagger and von Jagow, Anal. Biochem., 1987, 166, 368–379) and transferred to PVDF membrane for sequencing. Sequencing was carried out on an Applied Biosystems A431 automated sequencer.

Amplification of AMPK cDNA

Degenerate oligonucleotides were synthesised corresponding to the N- and C-terminal sequences of peptide EL1. These oligonucleotides were then used to obtain the cDNA sequence that encodes EL1. Rat liver mRNA (1 µg) was reversed transcribed with a mixture of oligo dT and random hexamer primers (BRL Pre-Amplification kit). An aliquot of this reaction was diluted (1:100) and used in a polymerase chain reaction with the following primers: 5' NNNCCNGA (A/G) AA (C/T) GTN (C/T) TN (A/C/T) (C/T) NGA 3' (sense) SEQ ID NO:4 and 5' CAT (A/G) TTN (C/G) (A/T) NA (A/G) NCC (A/G) AA (A/G) TCNGC 3' (antisense) SEQ ID NO: for 40 cycles of 94° C., for 2 min: 55° C., 2 mins: 72° C., 2 min. The products of this reaction were diluted (1:200) and used for a second round of amplification (same conditions as before with "nested" primers: 5' CCNGA (A/G) AA (C/T) GTN (C/T) TN (A/C/T) (C/T) G 3' (sense) (SEQ ID NO:6) and 5' (A/G) TTN (C/G) (A/T) NA (A/G) NCC (A/G) AA (A/G) TCNGC (A/G) TC 3' (antisense) (SEQ ID NO:10). The products of the reaction were analysed by electrophoresis on a low-melting point agarose gel and a band of the expected size (63 nt) identified by ethidium bromide staining. The DNA was purified from the gel, blunt-ended with T4-polymerase and ligated into Bluescript. Plasmids containing an insert weRe identified by restriction digestion and sequenced by dideoxy chain termination (Sanger et al., 1977) using Sequenase 2.0 and vector primers.

Isolation of AMPK cDNA clones

Standard molecular biology techniques were used (Sambrook et al., 1989). A unique oligonucleotide (5' GACGCCCAGATGAATGCTAAG 3') SEQ ID NO:14 based on the sequence of the PCR product was used to probe a rat liver cDNA library (lambdaZAP II, Stratagene). Hybridisation conditions were: 30 ng probe (~$10^9$ c.p.m/ug; $10^6$ c.p.m/ml) in 5×SSPE, 100 ug/ml sonicated and denatured salmon sperm DNA, 2×Denharts, 0.1% SDS at 50° C. for 4 hours. Filters were washed with 5×SSC, 0.1% SDS at room temperature for 2 hours, followed by 5×SSC, 0.1% SDS at 50° C. for 30 min and autoradiography for 18 hours at −70° C. with intensifying screens. A total of 1.5×$10^6$ plaques were screened and eleven hybridising clones were isolated. Plasmids were recovered by in vivo excision from the phage (Short et al., Nucl. Acid. Res., 1988, 16, 7583–7600). Analysis of the inserts by restriction endonuclease mapping revealed that the clones could be divided into two groups: clones PK-$1_{1-8}$ (8 clones) contained an insert of ~2.6 kb, whilst clones PK-$2_{9-11}$ (3 clones) had an insert of ~2.7 kb. The inserts from both sets of clones were sequenced on both strands with either vector or AMPK cDNA specific primers.

Preparation of pBS-APK

In order to obtain a cDNA clone containing the entire coding sequence of AMPK, rat liver cDNA was amplified using primers based on clones PK-1 and PK-2 (foward primer-5' GCCGAACATGGCTGAGAAG 3' nt 1–19: (SEQ ID NO:15) reverse primer-5' TCTTAGCATTCATCTGGGC 3'; antisense nt 452–470) (SEQ ID NO:16). The larger of the products was purified by electrophoresis on a low-melting point agarose gel, recovered using Magic DNA clean-up resin (Promega), cloned into Bluescript and sequenced to confirm the orientation and identity of the insert. This plasmid was then digested with NotI and BglII to release a fragment of ~185 bp. The notI-BglII fragment was purified and ligated into PK-1 that had been digested with NotI and BglII. The resulting clone (pBS-APK) was isolated and sequenced across the NotI-BglII region to verify its integrity.

RNA analysis

Total RNA was isolated from various rat tissues (Chomczynski and Saachi, 1987). RNA (1 μg) was reverse transcribed with AMV-RT at 42° C. for 30 min. using random hexamers. An aliquot of this reaction was used in PCR with various AMPK specific primers under the following conditions; initial denaturing step of 94° C. for 3 min. followed by 30 cycles of 94° C., 1 min; 55° C., 1 min; 72°, 1 min. Products were analysed by electrophoresis on agarose gels. Rat multiple tissue Northern (Clontech) was probed with either a random primed (Feinberg and Volgelstein, Anal. Biochem., 1983, 132, 6–13) 1.9 kb EcoRI fragment from pBS-APK, or a rat GAPDH fragment, according to the manufacturers instructions. The blot was washed with 2×SSC, 0.5% SDS at room temperature for 1 hour, followed by 0.2×SSC. 0.5% SCS at 65° C. for 2×20 min.

Southern blotting

Rat genomic DNA (10 μg) was digested overnight at 37° C. with various restriction endonucleases. DNA was electrophoresed on a 1% agarose gel and tranferred to a nylon membrane (GT membrane, Bio-Rad). The membrane was probed with the entire insert from clone PK 1 using the following hybridisation conditions: 5×SSPE, 100 μg/ml sonicated and denatured salmon sperm DNA, 2×Denhardts, 0.1% SDS, 50% formamide at 42° C. for 16 hours. Filters were washed with 2×SSC, 0.5% SDS at room temperature for 1 hour followed by 0.1×SSC, 0.5% SDS at 65° C. for 2×20 min.

Expression of AMPK using the baculovirus system

The 1.9 kb EcoRI fragment pBS-APK was inserted into the baculovirus transfer vector, pVL1392 (AMS Biotechnology). The correct orientation of the insert was determined by digestion with BamHI yielding the recombinant vector, pVL-APK. Approximately 2 μg pVL-AMP (purified by caesium chloride density gradient centrifugation) and 1 μg BaculoGold linearised baculovirus DNA (AMS Biotechnology) was co-transfected into Sf9 cells using calcium phosphate preciptation. Recombinant viral particles were amplified through two rounds of infection, before infecting a large scale preparation of insect cells ($10^9$ cells: m.o.i. 10). Cells were grown at 27° C. and were harvested just prior to lysis (approximately 72 hours). After centrifugation cells were lysed by resuspension in 50 mM Tris-HCl (pH 7.5), 50 mM NaF, 5 mM Napyrophosphate, 1 mM EDTA, 1 mM DTT, 0.1 mM PMSF, 10% (v/v) glycerol (buffer A) containing 1% Triton-X 100. The resulting material was centrifuged at 10,000×g for 15 min. For metabolic labelling Sf9 cells were incubated with [$^{35}$S] methionine for 1 hour, 72 hours post-infection, and lysed as above. The supernatant fraction was used for immunopreciptation of recombinant AMPK.

We claim:

1. A recombinant polypeptide fragment of an AMP protein kinase, said fragment comprising at least 21 contiguous amino acids from an amino acid sequence selected from the group consisting of human AMP protein kinase encoded by the nucleic acid sequence depicted in SEQ ID NO:37 and rat AMP protein kinase encoded by the nucleic acid sequence depicted in SEQ ID NO:38.

2. The recombinant polypeptide fragment according to claim 1, said fragment having the ability to induce antibodies specific for a polypeptide selected from the group consisting of human AMP protein kinase and rat AMP protein kinase.

3. The recombinant polypeptide fragment according to claim 1, wherein the synthetic polypeptide has AMP protein kinase enzymatic activity.

4. The recombinant polypeptide fragment according to claim 1, which comprises at least 21 contiguous amino acids from human AMP protein kinase encoded by the nucleic acid sequence depicted in SEQ ID NO:37.

5. The recombinant polypeptide fragment according to claim 1, which comprises at least 21 contiguous amino acids from rat AMP protein kinase encoded by the nucleic acid sequence depicted in SEQ ID NO:38.

6. A fusion protein having mammalian AMP protein kinase enzymatic activity, said fusion protein comprising human AMP protein kinase encoded by the nucleic acid sequence depicted in SEQ ID NO:37 or rat AMP protein kinase encoded by the nucleic acid sequence depicted in SEQ ID NO:38.

7. A recombinant polypeptide comprising human AMP protein kinase encoded by SEQ ID NO:37, wherein the recombinant polypeptide is a fusion protein.

8. A recombinant polypeptide comprising rat AMP protein kinase encoded by SEQ ID NO:38, wherein the recombinant polypeptide is a fusion protein.

9. A cDNA encoding a mammalian AMP protein kinase, selected from the group consisting of SEQ ID NO:37 and SEQ ID NO:38.

10. The cDNA according to claim 9, wherein the mammalian AMP protein kinase is a human AMP protein kinase, which is encoded by SEQ ID NO:37.

11. The cDNA according to claim 9, wherein the mammalian AMP protein kinase is a rat AMP protein kinase, which is encoded by SEQ ID NO:38.

12. A process of producing a recombinant polypeptide fragment of AMP protein kinase, said fragment comprising at least 21 contiguous amino acids from an amino acid sequence selected from the group consisting of human AMP protein kinase encoded by the nucleic acid sequence depicted in SEQ ID NO:37 and rat AMP protein kinase encoded by the nucleic acid sequence depicted in SEQ ID NO:38, said fragment having mammalian AMP protein kinase enzymatic activity, said method comprising:

(a) introducing a nucleic acid encoding the polypeptide fragment having mammalian AMP protein kinase enzymatic activity into a host cell; and (b) expressing the polypeptide fragment in the host cell.

13. The process according to claim 12, further comprising purifying the recombinant polypeptide fragment from the host cell.

14. The process according to claim 12, wherein the host cell is an Sf9 cell.

15. A process of screening for a desired agent which modulates mammalian protein kinase activity comprising:

(a) producing an AMP protein kinase according to the method of claim 12;

(b) contacting a potential agent with the recombinant polypeptide or the host cell expressing the gene; and (c) identifying the desired agent by modulation of mammalian protein kinase activity.

16. The process according to claim 15, wherein the desired agent reduces biosynthesis of cholesterol and fatty acids.

17. The process according to claim 15, wherein the desired agent inhibits release of cholesterol and fatty acids from intracellular stores by hormone sensitive lipase.

18. The process according to claim 15, wherein the potential agent is contacted with the recombinant polypeptide and the desired agent increases mammalian protein kinase activity.

19. The process according to claim 15, wherein the potential agent is contacted with the host cell expressing the gene and the desired agent increases expression of mammalian protein kinase.

20. Purified or partially purified antibodies raised against the recombinant polypeptide fragment according to claim 1.

* * * * *

SEQUENCE LISTING (1) GENERAL INFORMATION:

(iii) NUMBER OF SEQUENCES: 40

(2) INFORMATION FOR SEQ ID NO: 1:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO: 1:

```
Xaa Leu Xaa Pro Glu Asn Val Leu Xaa Asp Ala Xaa Met Asn Ala
 1               5                  10                  15

Xaa Asp Ala Asp Phe Gly Leu Ser Asn Met
                20                  25
```

(2) INFORMATION FOR SEQ ID NO: 2:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO: 2:

```
Leu Lys Leu Arg Pro Leu Tyr Asp Ile Pro Tyr His Phe Glu Ala
 1               5                  10                  15

Arg Glu Phe Leu Arg
                20
```

(2) INFORMATION FOR SEQ ID NO: 3:

(i) SEQUENCE CHARACTERISTICS:

```
            (A) LENGTH: 27 amino acids
            (B) TYPE: amino acid
            (C) STRANDEDNESS: single
            (D) TOPOLOGY: linear (xi) SEQUENCE DESCRIPTION: SEQ ID NO: 3:

Ala Thr Xaa Xaa Thr Xaa Glu Leu Val Leu Gln Arg Glu Val Glu
 1               5                  10                  15

Val Glu Val Glu Ser Met Asp Lys Ala Gly Asn Phe
                20                  25

(2) INFORMATION FOR SEQ ID NO: 4:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO: 4:

NNNCCNGARA AYGTNYTNNY NGA                                          23

(2) INFORMATION FOR SEQ ID NO: 5:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO: 5:

Xaa Pro Glu Asn Val Leu Thr Leu Asp
 1               5

(2) INFORMATION FOR SEQ ID NO: 6:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO: 6:

CCNGARAAYG TNYTNHYNGA YG                                           22

(2) INFORMATION FOR SEQ ID NO: 7:

(i) SEQUENCE CHARACTERISTICS:
            (A) LENGTH: 9 amino acids
            (B) TYPE: amino acid
            (C) STRANDEDNESS: single
            (D) TOPOLOGY: linear (xi) SEQUENCE DESCRIPTION: SEQ ID NO: 7:

Pro Glu Asn Val Leu Thr Leu Asp Ala
 1               5

(2) INFORMATION FOR SEQ ID NO: 8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 8:

CATRTTNSWN ARNCCRAART CNGC                                         24
```

(2) INFORMATION FOR SEQ ID NO: 9:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 9:

```
Met Asn Ser Leu Gly Phe Asp Ala
 1               5
```

(2) INFORMATION FOR SEQ ID NO: 10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 10:

```
RTTNSWNARN CCRAARTCNG CRTC                                           24
```

(2) INFORMATION FOR SEQ ID NO: 11:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 11:

```
Asn Ser Leu Gly Phe Asp Ala Asp
 1               5
```

(2) INFORMATION FOR SEQ ID NO: 12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 12:

```
GCCCAGATGA ATGCTAAG                                                  18
```

(2) INFORMATION FOR SEQ ID NO: 13:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 13:

```
Ala Pro Met Asn Ala Lys
 1               5
```

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 14:

```
GACGCCCAGA TGAATGCTAA G                                                     21
```

(2) INFORMATION FOR SEQ ID NO: 15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 15:

```
GCCGAACATG GCTGAGAAG                                                        19
```

(2) INFORMATION FOR SEQ ID NO: 16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 16:

```
TCTTAGCATT CATCTGGGC                                                        19
```

(2) INFORMATION FOR SEQ ID NO: 17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 17:

```
GAAGATCGGA CACTACG                                                          17
```

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 18:

```
CCTCCAGACA CATATTCC                                                         18
```

(2) INFORMATION FOR SEQ ID NO: 19:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 19:

```
Pro Glu Asp Pro Ser Tyr Asp Ala Asn Val Ile Asp Asp Glu
 1               5                  10
```

(2) INFORMATION FOR SEQ ID NO: 20:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 20:

```
Pro Gly Leu Lys Pro His Pro Glu Arg Met Pro Pro Leu Ile
  1               5                  10
```

(2) INFORMATION FOR SEQ ID NO: 21:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 21:

```
Val Val Glu Gln Arg Ser Gly Ser Ser Thr Pro Gln Arg Ser
  1               5                  10
```

(2) INFORMATION FOR SEQ ID NO: 22:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 22:

```
His Arg Pro Arg Ser Ser Val Asp Ser Ser Thr Ala Glu Asn
  1               5                  10
```

(2) INFORMATION FOR SEQ ID NO: 23:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO: 23:

```
His Met Arg Ser Ala Met Ser Gly Leu His Leu Val Lys Arg Arg
  1               5                  10                  15
```

(2) INFORMATION FOR SEQ ID NO: 24:

(i) SEQUENCE CHARACTERISTICS:
        (A) LENGTH: 2761 base pairs
        (B) TYPE: nucleic acid
        (C) STRANDEDNESS: single
        (D) TOPOLOGY: linear (xi) SEQUENCE DESCRIPTION: SEQ ID NO: 24:

```
CCCGGGGAGG CCGCGCGCCG AACATGGCTG AGAAGCAGAA GCACGACGGG CGTGTGAAGA      60

TCGGACACTA CGTGCTGGGG GACACCCTGG GCGTCGGCAC CTTCGGCAAA GTGAAGATTG     120

GAGAACATCA ATTGACAGGC CATAAAGTGG CAGTTAAGAT CTTAAATAGA CAGAAGATTC     180

GCAGTTTAGA TGTTGTTGGA AAAATAAAAC GAGAAATTCA AAATCTTAAA CTCTTTCGTC     240

ATCCTCATAT TATCAAACTC TACCAAGTGA TCAGCACTCC AACAGACTTT TTTATGGTAA     300

TGGAATATGT GTCTGGAGGT GAATTGTTCG ACTACATCTG TAAACACGGG AGGGTTGAAG     360

AGGTGGAAGC TCGCCGGCTC TTCCAGCAGA TTCTGTCTGC CGTGGACTAC TGTCACAGGC     420

ACATGGTTGT CCACAGGGAC CTGAAGCCAG AGAACGTGTT GCTGGACGCC AGATGAATG      480

CTAAGATAGC TGACTTCGGA CTCTCTAATA TGATGTCAGA TGGTGAATTT CTACGAACTA     540

GCTGTGGATC GCCAAATTAT GCAGCACCGG AGGTCATCTC AGGAAGGCTG TATGCGGGTC     600

CTGAGGTTGA TATCTGGAGC TGTGGTGTTA TCCTGTATGC CCTTCTCTGT GGCACCCTCC     660
```

```
CGTTCGACGA TGAGCACGTG CCTACGCTCT TTAAGAAGAT CCGAGGGGGT GTGTTCTACA      720

TCCCGGAGTA TCTCAACCGT TCTATTGCCA CTCTGCTGAT GCACATGCTG CAGGTGGACC      780

CCTTGAAGCG AGCAACTATC AAAGACATAC GAGAGCATGA ATGGTTTAAA CAGGATTTGC      840

CCAGTTACCT CTTTCCTGAA GACCCCTCCT ATGATGCTAA CGTCATTGAT GATGAGGCTG      900

TGAAAGAAGT ATGTGAAAAA TTTGAGTGTA CAGAATCAGA AGTGATGAAC AGTTTATACA      960

GTGGTGACCC TCAAGACCAG CTCGCAGTGG CTTATCATCT CATCATTGAC AATCGGAGAA     1020

TAATGAACCA AGCCAGTGAG TTCTACCTCG CCTCCAGTCC TCCAACGGGT TCCTTCATGG     1080

ACGATATGGC CATGCACATT CCCCCCGGCC TGAAACCACA TCCTGAAAGG ATGCCACCTC     1140

TCATAGCAGA CAGCCCCAAA GCACGCTGTC CACTGGATGC ACTCAACACA ACTAAGCCCA     1200

AATCTTTAGC TGTGAAAAAA GCCAAGTGGC ACCTTGGGAT CCGAAGCCAG AGCAAACCAT     1260

ACGACATTAT GGCGGAGGTG TACCGAGCTA TGAAGCAGCT GGACTTTGAA TGGAAGGTAG     1320

TGAATGCATA CCATCTTCGA GTAAGAAGAA AAAACCCAGT GACTGGCAAT TACGTGAAAA     1380

TGAGCTTACA GCTTTACCTG GTTGACAATC GGAGCTATCT TCTAGACTTT AAAAGCATCG     1440

ATGATGAGGT GGTGGAGCAG AGGTCTGGTT CTTCAACACC TCAGCGCTCC TGTTCTGCTG     1500

CCGGCCTCCA CAGACCTCGG TCAAGTGTCG ATTCCAGCAC AGCCGAGAAC CATTCACTGT     1560

CTGGCTCTCT CACTGGTTCT TTGACTGGCA GAACTTTGTC CTCCGCTTCC CCGCGCCTGG     1620

GCAGTCATAC CATGGATTTT TTTGAAATGT GCGCCAGTCT TATCACTGCT TTAGCCCGTT     1680

GATAACCCAC CACCGGTCTC TGTCTTTCTG TTACCGCACT GTGAAATCAC ATACACTCTT     1740

CAAATTATTA CCGCACTCTC GGGTACCACA GGCTCTGCAA TAGAAGTTAT GTGAACATTC     1800

CCAGGTGACA TGCAGTGCTG CTGGAAACAC AGAAATCTGG CCTTCTGTTT ACTTTTAGAA     1860

CTCTGTAACT CTGCTGTGCC TATGATAGGT ATCAATAGCT AGGAACGGCT GAGTGCTGGT     1920

GAAGCTTGTT AACTTACACC CGTGAATTCA CTACACATGG TGAGCACACC TCACTGATGA     1980

ACCCGCTGAT CTCGGGGTGG TTCGGTGGGA CCGCCTTCCT TCACGTTTAG TTCATGTAAA     2040

TCCTGTTTGC CTCCTAAATT CCATAGGTGT CAGGCTGTC TAGGCACTCT TGGACAAGAA     2100

GATTCAGAAA TAGAGTAACT GTCAGTGAAA TATTATTTAA ATGTAGAAAT CCGAAATCCT     2160

GTCCCCTTAA ATATCAGAAA CCAAAAGTCT TTTTTAATAC TTTCTGCAAA TACTGCCTAG     2220

TATTAGCCAT ACAGACTGTG TTTCTGATAA TAGGAGCCCA GTCTCCTAGC TTCCTGACAT     2280

TTGTGCAAGG CCCCTAGTTA AATCCCACTA CCACAAAGCA ATATAAAACC ATGCAAAGTT     2340

AGTGCATAGT TAAAGGAAAC AGGCAGATAC CAACAGTCTC TTAAAAGGAA ATCTATTCTT     2400

TGATCTCATT TGTGTTTATG AGACTGGGTA GCTGGGGCT TGGGGCGGG CTGGGAGTCA       2460

CAGCCCTTGG GCATCTTTGC TAATCCACTT GAACTTTGTT ATTGATGCCG AGTCCTCTCT     2520

CTTCCTCAGT AGCCACTGTC TTTGCTCATT GCTTTTCCCT TTTTTAACTC CTTTAGATCA     2580

AAACCTTGCT TTGGCCATAG GGTCTTTAAA TACTTTCAAA GCTTGATCTG CTGTGACCTT     2640

CACTGTTGAA CCTGATTGGA CAGGGAAGCC TTAAATATTT AAAAGTATAT TCTCCTGGAA     2700

TAACTACATG TGTTGTTTAC ATATATATAC ATATGTATTG ACACATCAGT GCTTTTAATC     2760

G                                                                    2761
```

(2) INFORMATION FOR SEQ ID NO: 25:

(i) SEQUENCE CHARACTERISTICS:
        (A) LENGTH: 27 amino acids
        (B) TYPE: amino acid
        (C) STRANDEDNESS: single (D) TOPOLOGY: linear (xi) SEQUENCE DESCRIPTION: SEQ ID NO: 25:

Xaa Leu Xaa Pro Glu Asn Val Leu Thr Leu Asp Ala Gln Pro Met
 1               5                  10                  15

Asn Ala Xaa Asp Ala Asp Phe Gly Leu Ser Asn Met
                20                  25

(2) INFORMATION FOR SEQ ID NO: 26:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO: 26:

Glu Tyr Val Tyr Gly Lys Leu Glu Leu Phe Ala Tyr Leu Xaa Lys
 1               5                  10                  15

Xaa Gly Xaa Xaa Xaa Xaa Val
                20

(2) INFORMATION FOR SEQ ID NO: 27:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO: 27:

Leu Gln Val Asp Pro Leu Lys Arg Ala Thr Ile Lys Asp Ile Xaa
 1               5                  10                  15

Glu Glu Glu Trp Phe Lys Gln
                20

(2) INFORMATION FOR SEQ ID NO: 28:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO: 28:

Pro Pro Leu Ile Ala Asp Xaa Pro Lys Ala Arg Xaa Pro Leu Asp
 1               5                  10                  15

Ala Leu Asn Thr Thr Lys
                20

(2) INFORMATION FOR SEQ ID NO: 29:

(i) SEQUENCE CHARACTERISTICS:
        (A) LENGTH: 25 amino acids
        (B) TYPE: amino acid
        (C) STRANDEDNESS: single
        (D) TOPOLOGY: linear (xi) SEQUENCE DESCRIPTION: SEQ ID NO: 29:

Lys Gln Leu Asp Phe Glu Trp Ser Lys Gly Lys Val Val Asn Ala
 1               5                  10                  15

Tyr His Leu Arg Val Arg Xaa Lys Xaa Asn
                20                  25

(2) INFORMATION FOR SEQ ID NO: 30:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO: 30:

Pro Glu Asn Val Leu Thr Asp Ala Gln Met Asn Ala Xaa Asp Ala
1               5                   10                  15

Asp Phe Gly Leu Ser Asn Met
                20

(2) INFORMATION FOR SEQ ID NO: 31:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO: 31:

Glu Asn Val Leu Leu Thr Asp Ala Gln Met Asn Ala Xaa Asp Ala
1               5                   10                  15

Asp Phe Gly Leu Ser Asn Met
                20

(2) INFORMATION FOR SEQ ID NO: 32:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 32:

Glu Phe Tyr Leu Ala
1               5

(2) INFORMATION FOR SEQ ID NO: 33:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO: 33:

Met Glu Tyr Val Ser Gly Gly Glu Leu Phe Asp Tyr Ile Cys Lys
1               5                   10                  15

His Gly Arg Val Glu Glu
                20

(2) INFORMATION FOR SEQ ID NO: 34:

(i) SEQUENCE CHARACTERISTICS:
        (A) LENGTH: 22 amino acids
        (B) TYPE: amino acid
        (C) STRANDEDNESS: single
        (D) TOPOLOGY: linear (xi) SEQUENCE DESCRIPTION: SEQ ID NO: 34:

Met Pro Pro Leu Ile Ala Asp Ser Pro Lys Ala Arg Cys Pro Leu
1               5                   10                  15

Asp Ala Leu Asn Thr Thr Lys

20

(2) INFORMATION FOR SEQ ID NO: 35:

(i) SEQUENCE CHARACTERISTICS:
        (A) LENGTH: 21 amino acids
        (B) TYPE: amino acid
        (C) STRANDEDNESS: single
        (D) TOPOLOGY: linear (xi) SEQUENCE DESCRIPTION: SEQ ID NO: 35:

```
Met Lys Gln Leu Asp Phe Glu Trp Lys Val Val Asn Ala Tyr His
 1               5                  10                  15

Leu Arg Val Arg Arg Lys
                20
```

(2) INFORMATION FOR SEQ ID NO: 36:

(i) SEQUENCE CHARACTERISTICS:
        (A) LENGTH: 1783 base pairs
        (B) TYPE: nucleic acid
        (C) STRANDEDNESS: single
        (D) TOPOLOGY: linear (xi) SEQUENCE DESCRIPTION: SEQ ID NO: 36:

```
GATGGCTGAG AAGCAGAAGC ACGACGGGCG GGTGAAGATC GGACACTACG TGCTGGGCGA      60
CACGCTGGGC GTCGGCACCT TCGGCAAAGT GAAGATTGGA GAACATCAAT TAACAGGCCA     120
TAAAGTGGCA GTTAAAATCT AAATAGACA GAAGATTCGC AGTTTAGATG TTGTTGGAAA     180
AATAAAACGA GAAATTCAAA ATCTAAAACT CTTTCGTCAT CCTCATATTA TCAAACTATA     240
CCAGGTGATC AGCACTCCAA CAGATTTTTT TATGGTAATG GAATATGTGT CTGGAGGTGA     300
ATTATTTGAC TACATCTGTA AGCATGGACG GGTTGAAGAG ATGGAAGCCA GGCGGCTCTT     360
TCAGCAGATT CTGTCTGCTG TGGATTACTG TCATAGGCAT ATGGTTGTTC ATCGAGACCT     420
GAAACCAGAG AATGTCCTGT TGGATGCACA CATGAATGCC AAGATAGCCG ATTTCGGATT     480
ATCTAATATG ATGTCAGATG GTGAATTTCT GAGAACTAGT TGCGGATCTC CAAATTATGC     540
AGCACCTGAA GTCATCTCAG GCAGATTGTA TGCAGGTCCT GAAGTTGATA TCTGGAGCTG     600
TGGTGTTATC TTGTATGCTC TTCTTTGTGG CACCCTCCCA TTTGATGATG AGCATGTACC     660
TACGTTATTT AAGAAGATCC GAGGGGGTGT CTTTTATATC CCAGAATATC TCAATCGTTC     720
TGTCGCCACT CTCCTGATGC ATATGCTGCA GGTTGACCCA CTGAAACGAG CAACTATCAA     780
AGACATAAGA GAGCATGAAT GGTTTAAACA AGATTTGCCC AGTTACTTAT TTCCTGAAGA     840
CCCTTCCTAT GATGCTAACG TCATTGATGA TGAGGCTGTG AAAGAAGTGT GTGAAAAATT     900
TGAATGTACA GAATCAGAAG TAATGAACAG TTTATATAGT GGTGACCCTC AAGACCAGCT     960
TGCAGTGGCT TATCATCTTA TCATTGACAA TCGGAGAATA ATGAACCAAG CCAGTGAGTT    1020
CTATCTCGCC TCTAGTCCTC CATCTGGTTC TTTTATGGAT GATAGTGCCA TGCATATTCC    1080
CCCAGGCCTG AAACCTCATC CAGAAAGGAT GCCACCTCTT ATAGCAGACA GCCCCAAAGC    1140
AAGATGTCCA TTGGATGCAC TGAATACGAC TAAGCCCAAA TCTTTAGCTG TGAAAAAAGC    1200
CAAGTGGCAT CTTGGAATCC GAAGTCGAGA CAAACCGTAT GACATTATGG CTGAAGTTTA    1260
CCGAGCTATG AAGCAGCTGG ATTTTGAATG GAAGGTAGTG AATGCATACC ATCTTCGTGT    1320
AAGAAGAAAA AATCCAGTGA CTGGCAATTA CGTGAAAATG AGCTTACAAC TTTACCTGGT    1380
TGATAACAGG AGCTATCTTT TGGACTTTAA AAGCATTGAT GATGAAGTAG TGGAGCAGAG    1440
ATCTGGTTCC TCAACACCTC AGCGTTCCTG TTCTGCTGCT GGCTTACACA GACCAAGATC    1500
```

```
AAGTTTTGAT TCCACAACTG CAGAGAGCCA TTCACTTTCT GGCTCTCTCA CTGGCTCTTT      1560

GACCGGAAGC ACATTGTCTT CAGTTTCACC TCGCCTGGGC AGTCACACCA TGGATTTTTT      1620

TGAAATGTGT GCCAGTCTGA TTACTACTTT AGCCCGTTGA TCTGTCTCTA GTTTCTTTCT      1680

GTTATTGCAC TATGAAAATC AGTTATATTC TTTAAATTTT TATCTTACTT TTGGATAATA      1740

TCCATCCAGC TTGGACTTAA CCAGGCTGAA CTTGCTCAAA AGG                       1783

(2) INFORMATION FOR SEQ ID NO: 37:

(i) SEQUENCE CHARACTERISTICS:
        (A) LENGTH: 1736 base pairs
        (B) TYPE: nucleic acid
        (C) STRANDEDNESS: single
        (D) TOPOLOGY: linear (xi) SEQUENCE DESCRIPTION: SEQ ID NO: 37:

ATGGCTGAGA AGCAGAAGCA CGACGGGCGG GTGAAGATCG GACACTACGT GCTGGGCGAC        60

ACGCTGGGCG TCGGCACCTT CGGCAAAGTG AAGATTGGAG AACATCAATT AACAGGCCAT       120

AAAGTGGCAG TTAAAATCTT AAATAGACAG AAGATTCGCA GTTTAGATGT TGTTGGAAAA       180

ATAAAACGAG AAATTCAAAA TCTAAAACTC TTTCGTCATC CTCATATTAT CAAACTATAC       240

CAGGTGATCA GCACTCCAAC AGATTTTTTT ATGGTAATGG AATATGTGTC TGGAGGTGAA       300

TTATTTGACT ACATCTGTAA GCATGGACGG GTTGAAGAGA TGGAAGCCAG GCGGCTCTTT       360

CAGCAGATTC TGTCTGCTGT GGATTACTGT CATAGGCATA TGGTTGTTCA TCGAGACCTG       420

AAACCAGAGA ATGTCCTGTT GGATGCACAC ATGAATGCCA AGATAGCCGA TTTCGGATTA       480

TCTAATATGA TGTCAGATGG TGAATTTCTG AGAACTAGTT GCGGATCTCC AAATTATGCA       540

GCACCTGAAG TCATCTCAGG CAGATTGTAT GCAGGTCCTG AAGTTGATAT CTGGAGCTGT       600

GGTGTTATCT TGTATGCTCT TCTTTGTGGC ACCCTCCCAT TTGATGATGA GCATGTACCT       660

ACGTTATTTA AGAAGATCCG AGGGGGTGTC TTTTATATCC CAGAATATCT CAATCGTTCT       720

GTCGCCACTC TCCTGATGCA TATGCTGCAG GTTGACCCAC TGAAACGAGC AACTATCAAA       780

GACATAAGAG AGCATGAATG GTTTAAACAA GATTTGCCCA GTTACTTATT TCCTGAAGAC       840

CCTTCCTATG ATGCTAACGT CATTGATGAT GAGGCTGTGA AGAAGTGTG TGAAAAATTT       900

CAATGTACAG AATCAGAAGT AATGAACAGT TTATATAGTG GTGACCCTCA AGACCAGCTT       960

GCAGTGGCTT ATCATCTTAT CATTGACAAT CGGAGAATAA TGAACCAAGC CAGTGAGTTC      1020

TATCTCGCCT CTAGTCCTCC ATCTGGTTCT TTTATGGATG ATAGTGCCAT GCATATTCCC      1080

CCAGGCCTGA AACCTCATCC AGAAAGGATG CCACCTCTTA TAGCAGACAG CCCCAAAGCA      1140

AGATGTCCAT TGGATGCACT GAATACGACT AAGCCCAAAT CTTTAGCTGT GAAAAAAGCC      1200

AAGTGGCATC TTGGAATCCG AAGTCAGAGC AAACCGTATG ACATTATGGC TGAAGTTTAC      1260

CGAGCTATGA AGCAGCTGGA TTTTGAATGG AAGGTAGTGA ATGCATACCA TCTTCGTGTA      1320

AGAAGAAAAA ATCCAGTGAC TGGCAATTAC GTGAAAATGA GCTTACAACT TTACCTGGTT      1380

GATAACAGGA GCTATCTTTT GGACTTTAAA AGCATTGATG ATGAAGTAGT GGAGCAGAGA      1440

TCTGGTTCCT CAACACCTCA GCGTTCCTGT TCTGCTGCTG GCTTACACAG ACCAAGATCA      1500

AGTTTTGATT CCACAACTGC AGAGAGCCAT TCACTTTCTG GCTCTCTCAC TGGCTCTTTG      1560

ACCGGAAGCA CATTGTCTTC AGTTTCACCT CGCCTGGGCA GTCACACCAT GGATTTTTTT      1620

GAAATGTGTG CCAGTCTGAT TACTACTTTA GCCCGTTGAT CTGTCTCTAG TTTCTTTCTG      1680

TTATTGCACT ATGAAAATCA GTTATATTCT TTAAATTTTT ATCTTACTTT TGGATA         1736
```

(2) INFORMATION FOR SEQ ID NO: 38:

(i) SEQUENCE CHARACTERISTICS:
        (A) LENGTH: 1742 base pairs
        (B) TYPE: nucleic acid
        (C) STRANDEDNESS: single
        (D) TOPOLOGY: linear (xi) SEQUENCE DESCRIPTION: SEQ ID NO: 38:

```
ATGGCTGAGA AGCAGAAGCA CGACGGGCGT GTGAAGATCG GACACTACGT GCTGGGGGAC      60
ACCCTGGGCG TCGGCACCTT CGGCAAAGTG AAGATTGGAG AACATCAATT GACAGGCCAT     120
AAAGTGGCAG TTAAGATCTT AAATAGACAG AAGATTCGCA GTTTAGATGT TGTTGGAAAA     180
ATAAAACGAG AAATTCAAAA TCTTAAACTC TTTCGTCATC CTCATATTAT CAAACTCTAC     240
CAAGTGATCA GCACTCCAAC AGACTTTTTT ATGGTAATGG AATATGTGTC TGGAGGTGAA     300
TTGTTCGACT ACATCTGTAA ACACGGGAGG GTTGAAGAGG TGGAAGCTCG CCGGCTCTTC     360
CAGCAGATTC TGTCTGCCGT GGACTACTGT CACAGGCACA TGGTTGTCCA CAGGGACCTG     420
AAGCCAGAGA ACGTGTTGCT GGACGCCCAG ATGAATGCTA AGATAGCTGA CTTCGGACTC     480
TCTAATATGA TGTCAGATGG TGAATTTCTA CGAACTAGCT GTGGATCGCC AAATTATGCA     540
GCACCGGAGG TCATCTCAGG AAGGCTGTAT GCGGGTCCTG AGGTTGATAT CTGGAGCTGT     600
GGTGTTATCC TGTATGCCCT TCTCTGTGGC ACCCTCCCGT TCGACGATGA GCACGTGCCT     660
ACGCTCTTTA AGAAGATCCG AGGGGGTGTG TTCTACATCC CGGAGTATCT CAACCGTTCT     720
ATTGCCACTC TGCTGATGCA CATGCTGCAG GTGGACCCCT TGAAGCGAGC AACTATCAAA     780
GACATACGAG AGCATGAATG GTTTAAACAG GATTTGCCCA GTTACCTCTT TCCTGAAGAC     840
CCCTCCTATG ATGCTAACGT CATTGATGAT GAGGCTGTGA AGAAGTATG TGAAAAATTT      900
GAGTGTACAG AATCAGAAGT GATGAACAGT TTATACAGTG GTGACCCTCA AGACCAGCTC     960
GCAGTGGCTT ATCATCTCAT CATTGACAAT CGGAGAATAA TGAACCAAGC CAGTGAGTTC    1020
TACCTCGCCT CCAGTCCTCC AACGGGTTCC TTCATGGACG ATATGGCCAT GCACATTCCC    1080
CCCGGCCTGA ACCACATCC TGAAAGGATG CCACCTCTCA TAGCAGACAG CCCCAAAGCA     1140
CGCTGTCCAC TGGATGCACT CAACACAACT AAGCCCAAAT CTTTAGCTGT GAAAAAAGCC    1200
AAGTGGCACC TTGGGATCCG AAGCCAGAGC AAACCATACG ACATTATGGC GGAGGTGTAC    1260
CGAGCTATGA AGCAGCTGGA CTTTGAATGG AAGGTAGTGA ATGCATACCA TCTTCGAGTA    1320
AGAAGAAAAA ACCCAGTGAC TGGCAATTAC GTGAAAATGA GCTTACAGCT TTACCTGGTT    1380
GACAATCGGA GCTATCTTCT AGACTTTAAA AGCATCGATG ATGAGGTGGT GGAGCAGAGG    1440
TCTGGTTCTT CAACACCTCA GCGCTCCTGT TCTGCTGCCG GCCTCCACAG ACCTCGGTCA    1500
AGTGTCGATT CCAGCACAGC CGAGAACCAT TCACTGTCTG GCTCTCTCAC TGGTTCTTTG    1560
ACTGGCAGAA CTTTGTCCTC CGCTTCCCCG CGCCTGGGCA GTCATACCAT GGATTTTTT     1620
GAAATGTGCG CCAGTCTTAT CACTGCTTTA GCCCGTTGAT AACCCACCAC CGGTCTCTGT    1680
CTTTCTGTTA CCGCACTGTG AAATCACATA CACTCTTCAA ATTATTACCG CACTCTCGGG    1740
TA                                                                    1742
```

(2) INFORMATION FOR SEQ ID NO: 39:

(i) SEQUENCE CHARACTERISTICS:
        (A) LENGTH: 2652 base pairs
        (B) TYPE: nucleic acid
        (C) STRANDEDNESS: single (D) TOPOLOGY: linear (xi) SEQUENCE DESCRIPTION: SEQ ID NO: 39:

```
GCCGAACATG GCTGAGAAGC AGAAGCACGA CGGGCGTGTG AAGATCGGAC ACTACGTGCT    60

GGGGGACACC CTGGGCGTCG GCACCTTCGG CAAAGTGAAG ATTGGAGAAC ATCAATTGAC   120

AGGCCATAAA GTGGCAGTTA AGATCTTAAA TAGACAGAAG ATTCGCAGTT TAGATGTTGT   180

TGGAAAAATA AAACGAGAAA TTCAAAATCT TAAACTCTTT CGTCATCCTC ATATTATCAA   240

ACTCTACCAA GTGATCAGCA CTCCAACAGA CTTTTTTATG GTAATGGAAT ATGTGTCTGG   300

AGGTGAATTG TTCGACTACA TCTGTAAACA CGGGAGGGTT GAAGAGGTGG AAGCTCGCCG   360

GCTCTTCCAG CAGATTCTGT CTGCCGTGGA CTACTGTCAC AGGCACATGG TTGTCCACAG   420

GGACCTGAAG CCAGAGAACG TGTTGCTGGA CGCCCAGATG AATGCTAAGA TAGCTGACTT   480

CGGACTCTCT AATATGATGT CAGATGGTGA ATTTCTACGA ACTAGCTGTG GATCGCCAAA   540

TTATGCAGCA CCGGAGGTCA TCTCAGGAAG GCTGTATGCG GGTCCTGAGG TTGATATCTG   600

GAGCTGTGGT GTTATCCTGT ATGCCCTTCT CTGTGGCACC CTCCCGTTCG ACGATGAGCA   660

CGTGCCTACG CTCTTTAAGA AGATCCGAGG GGGTGTGTTC TACATCCCGG AGTATCTCAA   720

CCGTTCTATT GCCACTCTGC TGATGCACAT GCTGCAGGTG GACCCCTTGA AGCGAGCAAC   780

TATCAAAGAC ATACGAGAGC ATGAATGGTT TAAACAGGAT TTGCCCAGTT ACCTCTTTCC   840

TGAAGACCCC TCCTATGATG CTAACGTCAT TGATGATGAG GCTGTGAAAG AAGTATGTGA   900

AAAATTTGAG TGTACAGAAT CAGAAGTGAT GAACAGTTTA TACAGTGGTG ACCCTCAAGA   960

CCAGCTCGCA GTGGCTTATC ATCTCATCAT TGACAATCGG AGAATAATGA ACCAAGCCAG  1020

TGAGTTCTAC CTCGCCTCCA GTCCTCCAAC GGGTTCCTTC ATGGACGATA TGGCCATGCA  1080

CATTCCCCCC GGCCTGAAAC CACATCCTGA AGGATGCCA CCTCTCATAG CAGACAGCCC  1140

CAAAGCACGC TGTCCACTGG ATGCACTCAA CACAACTAAG CCCAAATCTT TAGCTGTGAA  1200

AAAAGCCAAG TGGCACCTTG GGATCCGAAG CCAGAGCAAA CCATACGACA TTATGGCGGA  1260

GGTGTACCGA GCTATGAAGC AGCTGGACTT TGAATGGAAG GTAGTGAATG CATACCATCT  1320

TCGAGTAAGA AGAAAAAACC CAGTGACTGG CAATTACGTG AAAATGAGCT ACAGCTTTA  1380

CCTGGTTGAC AATCGGAGCT ATCTTCTAGA CTTTAAAAGC ATCGATGATG AGGTGGTGGA  1440

GCAGAGGTCT GGTTCTTCAA CACCTCAGCG CTCCTGTTCT GCTGCCGGCC TCCACAGACC  1500

TCGGTCAAGT GTCGATTCCA GCACAGCCGA GAACCATTCA CTGTCTGGCT CTCTCACTGG  1560

TTCTTTGACT GGCAGAACTT TGTCCTCCGC TTCCCCGCGC CTGGGCAGTC ATACCATGGA  1620

TTTTTTTGAA ATGTGCGCCA GTCTTATCAC TGCTTTAGCC CGTTGATAAC CCACCACCGG  1680

TCTCTGTCTT TCTGTTACCG CACTGTGAAA TCACATACAC TCTTCAAATT ATTACCGCAC  1740

TCTCGGGTAC CACAGGCTCT GCAATAGAAG TTATGTGAAC ATTCCCAGGT GACATGCAGT  1800

GCTGCTGGAA ACACAGAAAT CTGGCCTTCT GTTTACTTTT AGAACTCTGT AACTCTGCTG  1860

TGCCTATGAT AGGTATCAAT AGCTAGGAAC GGCTGAGTGC TGGTGAAGCT TGTTAACTTA  1920

CACCCGTGAA TTCACTACAC ATGGTGAGCA CACCTCACTG ATGAACCCGC TGATCTCGGG  1980

GTGGTTCGGT GGGACCGCCT TCCTTCACGT TTAGTTCATG TAAATCCTGT TTGCCTCCTA  2040

AATTTCCATA GGTGTCAGGC TGTCTAGGCA CTCTTGGACA AGAAGATTCA GAAATAGAGT  2100

AACTGTCAGT GAAATATTAT TTAAATGTAG AAATCCGAAA ATCCTGTCCC CTTAAATATC  2160

AGAAACCAAA AGTCTTTTTT AATACTTTCT GCAAATACTG CCTAGTATTA GCCATACAGA  2220

CTGTGTTTCT GATAATAGGA GCCCAGTCTC CTAGCTTCCT GACATTTGTG CAAGGCCCCT  2280
```

-continued

```
AGTTAAATCC CACTACCACA AAGCAATATA AAACCATGCA AAGTTAGTGC ATAGTTAAAG      2340

GAAACAGGCA GATACCAACA GTCTCTTAAA AGGAAATCTA TTCTTTGATC TCATTTGTGT      2400

TTATGAGACT GGGTAGCTGG GGGCTTGGGG GCGGGCTGGG AGTCACAGCC CTTGGGCATC      2460

TTTGCTAATC CACTTGAACT TTGTTATTGA TGCCGAGTCC TCTCTCTTCC TCAGTAGCCA      2520

CTGTCTTTGC TCATTGCTTT TCCCTTTTTT AACTCCTTTA GATCAAAACC TTGCTTTGGC      2580

CATAGGGTCT TTAAATACTT TCAAAGCTTG ATCTGCTGTG ACCTTCACTG TTGAACCTGA      2640

TTGGACAGGG AA                                                         2652
```

(2) INFORMATION FOR SEQ ID NO: 40:

(i) SEQUENCE CHARACTERISTICS:
        (A) LENGTH: 552 amino acids
        (B) TYPE: amino acid
        (C) STRANDEDNESS: single
        (D) TOPOLOGY: linear (xi) SEQUENCE DESCRIPTION: SEQ ID NO: 40:

```
Met Ala Glu Lys Gln Lys His Asp Gly Arg Val Lys Ile Gly His
 1               5                  10                  15

Tyr Val Leu Gly Asp Thr Leu Gly Val Gly Thr Phe Gly Lys Val
                20                  25                  30

Lys Ile Gly Glu His Gln Leu Thr Gly His Lys Val Ala Val Lys
                35                  40                  45

Ile Leu Asn Arg Gln Lys Ile Arg Ser Leu Asp Val Val Gly Lys
                50                  55                  60

Ile Lys Arg Glu Ile Gln Asn Leu Lys Leu Phe Arg His Pro His
                65                  70                  75

Ile Ile Lys Leu Tyr Gln Val Ile Ser Thr Pro Thr Asp Phe Phe
                80                  85                  90

Met Val Met Glu Tyr Val Ser Gly Gly Glu Leu Phe Asp Tyr Ile
                95                 100                 105

Cys His His Gly Arg Val Glu Glu Val Glu Ala Arg Arg Leu Phe
               110                 115                 120

Gln Gln Ile Leu Ser Ala Val Asp Tyr Cys His Arg His Met Val
               125                 130                 135

Val His Arg Asp Leu Lys Pro Glu Asn Val Leu Leu Asp Ala Gln
               140                 145                 150

Met Asn Ala Lys Ile Ala Asp Phe Gly Leu Ser Asn Met Met Ser
               155                 160                 165

Asp Gly Glu Phe Leu Arg Thr Ser Cys Gly Ser Pro Asn Tyr Ala
               170                 175                 180

Ala Pro Glu Val Ile Ser Gly Arg Leu Tyr Ala Gly Pro Glu Val
               185                 190                 195

Asp Ile Trp Ser Cys Gly Val Ile Leu Tyr Ala Leu Leu Cys Gly
               200                 205                 210

Thr Leu Pro Phe Asp Asp Glu His Val Pro Thr Leu Phe Lys Lys
               215                 220                 225

Ile Arg Gly Gly Val Phe Tyr Ile Pro Glu Tyr Leu Asn Arg Ser
               230                 235                 240

Ile Ala Thr Leu Leu Met His Met Leu Gln Val Asp Pro Leu Lys
               245                 250                 255

Arg Ala Thr Ile Lys Asp Ile Arg Glu His Glu Trp Phe Lys Gln
               260                 265                 270
```

```
Asp Leu Pro Ser Tyr Leu Phe Pro Glu Asp Pro Ser Tyr Asp Ala
            275                 280                 285

Asn Val Ile Asp Asp Glu Ala Val Lys Glu Val Cys Glu Lys Phe
            290                 295                 300

Glu Cys Thr Glu Ser Glu Val Met Asn Ser Leu Tyr Ser Gly Asp
            305                 310                 315

Pro Gln Asp Gln Leu Ala Val Ala Tyr His Leu Ile Ile Asp Asn
            320                 325                 330

Arg Arg Ile Met Asn Gln Ala Ser Glu Phe Tyr Leu Ala Ser Ser
            335                 340                 345

Pro Pro Thr Gly Ser Phe Met Asp Asp Met Ala Met His Ile Pro
            350                 355                 360

Pro Gly Leu Lys Pro His Pro Glu Arg Met Pro Pro Leu Ile Ala
            365                 370                 375

Asp Ser Pro Lys Ala Arg Cys Pro Leu Asp Ala Leu Asn Thr Thr
            380                 385                 390

Lys Pro Lys Ser Leu Ala Val Lys Lys Ala Lys Trp His Leu Gly
            395                 400                 405

Ile Arg Ser Gln Ser Lys Pro Tyr Asp Ile Met Ala Glu Val Tyr
            410                 415                 420

Arg Ala Met Lys Gln Leu Asp Phe Glu Trp Lys Val Val Asn Ala
            425                 430                 435

Tyr His Leu Arg Val Arg Arg Lys Asn Pro Val Thr Gly Asn Tyr
            440                 445                 450

Val Lys Met Ser Leu Gln Leu Tyr Leu Val Asp Asn Arg Ser Tyr
            455                 460                 465

Leu Leu Asp Phe Lys Ser Ile Asp Asp Glu Val Val Glu Gln Arg
            470                 475                 480

Ser Gly Ser Ser Thr Pro Gln Arg Ser Cys Ser Ala Ala Gly Leu
            485                 490                 495

His Arg Pro Arg Ser Ser Val Asp Ser Ser Thr Ala Glu Asn His
            500                 505                 510

Ser Leu Ser Gly Ser Leu Thr Gly Ser Leu Thr Gly Ser Thr Leu
            515                 520                 525

Ser Ser Ala Ser Pro Arg Leu Gly Ser His Thr Met Asp Phe Phe
            530                 535                 540

Glu Met Cys Ala Ser Leu Ile Thr Ala Leu Ala Arg
            545                 550
```